(12) United States Patent
Fu et al.

(10) Patent No.: US 11,672,832 B2
(45) Date of Patent: Jun. 13, 2023

(54) DEVELOPMENT OF AMNION-LIKE TISSUE FROM HUMAN PLURIPOTENT STEM CELLS

(71) Applicant: THE REGENTS OF THE UNIVERSITY OF MICHIGAN, Ann Arbor, MI (US)

(72) Inventors: Jianping Fu, Ann Arbor, MI (US); Deborah Gumucio, Ann Arbor, MI (US); Yue Shao, Ann Arbor, MI (US); Kenichiro Taniguchi, Ann Arbor, MI (US); Yi Zheng, Ann Arbor, MI (US); Sajedeh Nasr Esfahani, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 294 days.

(21) Appl. No.: 16/467,154

(22) PCT Filed: Dec. 8, 2017

(86) PCT No.: PCT/US2017/065261
§ 371 (c)(1),
(2) Date: Jun. 6, 2019

(87) PCT Pub. No.: WO2018/106997
PCT Pub. Date: Jun. 14, 2018

(65) Prior Publication Data
US 2019/0321415 A1 Oct. 24, 2019

Related U.S. Application Data

(60) Provisional application No. 62/431,907, filed on Dec. 9, 2016.

(51) Int. Cl.
| | |
|---|---|
| *A61K 35/545* | (2015.01) |
| *C12N 5/073* | (2010.01) |
| *A61K 31/74* | (2006.01) |
| *A61K 35/50* | (2015.01) |
| *C12N 5/00* | (2006.01) |
| *G01N 33/50* | (2006.01) |

(52) U.S. Cl.
CPC ............ *A61K 35/545* (2013.01); *A61K 31/74* (2013.01); *A61K 35/50* (2013.01); *C12N 5/0068* (2013.01); *C12N 5/0605* (2013.01); *G01N 33/5044* (2013.01); *C12N 2502/45* (2013.01); *C12N 2533/30* (2013.01)

(58) Field of Classification Search
CPC ...... A61K 35/545; A61K 31/74; A61K 35/50; C12N 5/0068; C12N 5/0605; C12N 2502/45; C12N 2533/30; G01N 33/5044
See application file for complete search history.

(56) References Cited

PUBLICATIONS

Romito A, Cobellis G. Pluripotent Stem Cells: Current Understanding and Future Directions. Stem Cells Int. 2016;2016:9451492 (Year: 2016).*
Shahbazi MN, Jedrusik A, Vuoristo S, Recher G, Hupalowska A, Bolton V, Fogarty NNM, Campbell A, Devito L, Ilic D, Khalaf Y, Niakan KK, Fishel S, Zernicka-Goetz M. Self-organization of the human embryo in the absence of maternal tissues. Nat Cell Biol. Jun. 2016;18(6):700-708. (Year: 2016).*
Mi S, David AL, Chowdhury B, et al. Tissue engineering a fetal membrane. Tissue Eng Part A. 2012;18(3-4):373-381. (Year: 2012).*
Fu J, Wang YK, Yang MT, Desai RA, Yu X, Liu Z, Chen CS. Mechanical regulation of cell function with geometrically modulated elastomeric substrates. Nat Methods. Sep. 2010;7(9):733-6. (Year: 2010).*
Shin Y, Han S, Jeon JS, et al. Microfluidic assay for simultaneous culture of multiple cell types on surfaces or within hydrogels. Nat Protoc. 2012;7(7):1247-1259. (Year: 2012).*
Lesher-Perez SC, Frampton JP, Takayama S. Microfluidic systems: a new toolbox for pluripotent stem cells. Biotechnol J. Feb. 2013;8(2):180-91. (Year: 2013).*
Miki T, Lehmann T, Cai H, Stolz DB, Strom SC. Stem cell characteristics of amniotic epithelial cells. Stem Cells. Nov.-Dec. 2005;23(10):1549-59. (Year: 2005).*
Lakins et al., Exploring the link between human embryonic stem cell organization and fate using tension-calibrated extracellular matrix functionalized polyacrylamide gels, Chapter 24 in Progenitor Cells Method and Protocols, Springer Protocols, Mace et al., editors, p. 317-350. (Year: 2012).*
Wang et al., Primary hepatocyte culture in collagen gel mixture and collagen sandwich, World Journal of Gastroenterology, 10(5): 699-702. (Year: 2004).*
Angello et al., Cell enlargement: one possible mechanism underlying cellular senescence, Journal of Cellular Physiology, 140: 288-294. (Year: 1989).*
Rossant, Stem cells from the mammalian blastocyst, Stem Cells, 19:477-482 (Year: 2001).*
International Search Report and Written Opinion for PCT/US17/65261. dated Feb. 23, 2018. 9 pages.
Bernardo et al., BRACHYURY and CDX2 mediate BMP-induced differentiation of human and mouse pluripotent stem cells into embryonic and extraembryonic lineages. Cell Stem Cell. Aug. 5, 2011;9(2):144-55.
Chang et al., Smad5 knockout mice die at mid-gestation due to multiple embryonic and extraembryonic defects. Development. Apr. 1999;126(8):1631-42.
Deglincerti et al., Self-organization of the in vitro attached human embryo. Nature. May 12, 2016;533(7602):251-4.

(Continued)

*Primary Examiner* — Laura Schuberg
*Assistant Examiner* — Joseph Paul Miano
(74) *Attorney, Agent, or Firm* — Casimir Jones, S.C.; Tanya A. Arenson

(57) ABSTRACT

The present disclosure provides compositions and methods employing stem cell-derived amnion tissue. In some embodiments, compositions (e.g., scaffolds and devices) and methods of generating amnion-like tissues from hPSCs are provided. In some embodiments, uses of such cells for research, compound screening and analysis, and therapeutics are provided.

6 Claims, 22 Drawing Sheets

(56) References Cited

PUBLICATIONS

Dobreva et al., On the origin of amniotic stem cells: of mice and men. Int J Dev Biol. 2010;54(5):761-77.

Dobreva et al., Periostin as a biomarker of the amniotic membrane. Stem Cells Int. 2012;2012:987185. 11 pages.

Faial et al., Brachyury and SMAD signalling collaboratively orchestrate distinct mesoderm and endoderm gene regulatory networks in differentiating human embryonic stem cells. Development. Jun. 15, 2015;142(12):2121-35.

Ferner et al., Evolution and development of fetal membranes and placentation in amniote vertebrates. Respir Physiol Neurobiol. Aug. 31, 2011;178(1):39-50.

Fu et al., Mechanical regulation of cell function with geometrically modulate elastomeric substrates. Nat Methods. Sep. 2010;7(9):733-6.

Gramignoli et al., Generation of induced Pluripotent Stem Cells from Human Amnion Epithelium. Placenta. Oct. 2011, vol. 32, Supplement 4, p. s334; abstract. 1 page.

Henderson et al., Preimplantation human embryos and embryonic stem cells show comparable expression of stage-specific embryonic antigens. Stem Cells. 2002;20(4):329-37.

Lancaster et al., Cerebral organoids model human brain development and microcephaly. Nature. Sep. 19, 2013;501(7467):373-9.

Lee et al., What is Trophoblast? a Combination of Criteria Define Human First-Trimester Trophoblast. Stem Cell Reports. Feb. 9, 2016;6(2):257-72.

Li et al., BMP4-directed trophoblast differentiation of human embryonic stem cells is mediated through a ΔNp63+ cytotrophoblast stem cell state. Development. Oct. 2013;140(19):3965-76.

Luckett, The development of primordial and definitive amniotic cavities in early Rhesus monkey and human embryos. Am J Anat. Oct. 1975;144(2):149-67.

Mallon et al., StemCellDB: the human pluripotent stem cell database at the National Institutes of Health. Stem Cell Res. Jan. 2013;10(1):57-66.

Mendjan et al., NANOG and CDX2 pattern distinct subtypes of human mesoderm during exit from pluripotency. Cell Stem Cell. Sep. 4, 2014;15(3):310-325.

Ml et al., Tissue Engineering a Fetal Membrane. Tissue Eng Part A. Feb. 2012; 18(3-4):373-81.

Miki et al., Amnion-derived pluripotent/multipotent stem cells. Stem Cell Rev. 2006;2(2):133-42.

Nakamura et al., A developmental coordinate of pluripotency among mice, monkeys and humans. Nature. Sep. 1, 2016;537(7618):57-62.

Nakano et al., Self-formation of optic cups and storable stratified neural retina from human ESCs. Cell Stem Cell. Jun. 14, 2012;10(6):771-785.

O'Leary et al., Tracking the progression of the human inner cell mass during embryonic stem cell derivation. Nat Biotechnol. Feb. 26, 2012;30(3):278-82.

Pereira et al., Amnion formation in the mouse embryo: the single amniochorionic fold model. BMC Dev Biol. Aug. 1, 2011;11:48. 13 pages.

Regauer et al., Intermediate filament cytoskeleton of amnion epithelium and cultured amnion epithelial cells: expression of epidermal cytokeratins in cells of a simple epithelium. J Cell Biol. Apr. 1985;100(4):997-1009.

Roost et al., KeyGenes, a Tool to Probe Tissue Differentiation Using a Human Fetal Transcriptional Atlas. Stem Cell Reports. Jun. 9, 2015;4(6):1112-24.

Sasaki et al., The Germ Cell Fate of Cynomolgus Monkeys is Specified in the Nascent Amnion. Dev Cell. Oct. 2, 20164;39(2):169-185.

Shahbazi et al., Self-organization of the human embryo in the absence of maternal tissues. Nat Cell Biol. Jun. 2016;18(6):700-708.

Shao et al., Self-organized amniogenesis by human pluripotent stem cells in a biomimetic implantation-like niche. Nat Mater. Apr. 2017;16(4):419-425.

Slieker et al., DNA Methylation Landscapes of Human Fetal Development. PLoS Genet. Oct. 22, 2015;11 (10):e1005583. 19 pages.

Takasato et al., Kidney organoids from human iPS cells contain multiple lineages and model human nephrogenesis. Nature. Oct. 22, 2015;526(7574):564-8.

Taniguchi et al., Lumen Formation is an Intrinsic Property of Isolated Human Pluripotent Stem Cells. Stem Cell Reports. Dec. 8, 2015;5(6):954-962.

Warmflash et al., A method to recapitulate early embryonic spatial patterning in human embryonic stem cells. Nat Methods. Aug. 2014;11(8):847-54.

Yan et al., Single-cell RNA-Seq profiling of human preimplantation embryos and embryonic stem cells. Nat Struct Mol Biol. Sep. 2013;20(9):1131-9.

Zhang et al., Mice deficient for BMP2 are nonviable and have defects in amnion/chorion and cardiac development. Development. Oct. 1996;122(10):2977-86.

\* cited by examiner

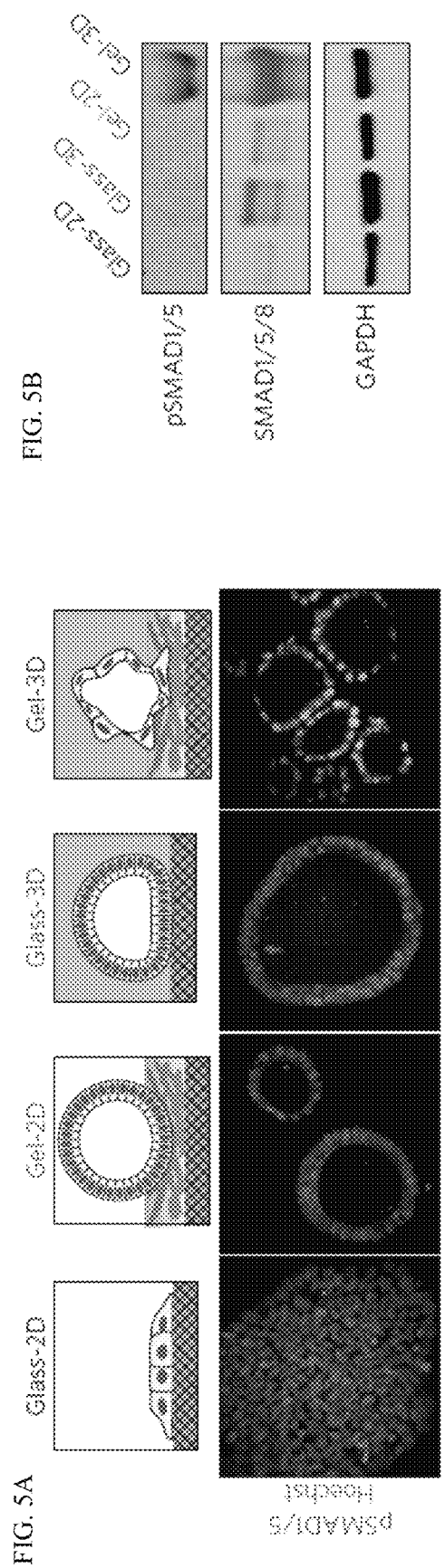

DEVELOPMENT OF AMNION-LIKE TISSUE FROM HUMAN PLURIPOTENT STEM CELLS

CROSS REFERENCE TO RELATED APPLICATIONS

This application is a U.S. 371 national phase entry of International Patent Application No. PCT/US2017/065261, filed Dec. 8, 2017, which claims the benefit of U.S. Provisional Application No. 62/431,907, filed Dec. 9, 2016, each of which is incorporated herein by reference in its entirety

STATEMENT REGARDING FEDERALLY SPONSORED RESEARCH OR DEVELOPMENT

The invention was made with government support under grant CBET1149401 awarded by the National Science Foundation, and grant EB019436 awarded by the National Institutes of Health. The government has certain rights in the invention.

FIELD

The present disclosure provides compositions and methods employing stem cell-derived amnion tissue. In some embodiments, compositions (e.g., scaffolds and devices) and methods of generating amnion-like tissues from human pluripotent stem cells (hPSCs) are provided. In some embodiments, uses of such cells for research, compound screening and analysis, and therapeutics are provided.

BACKGROUND

Stem cells are pluripotent cells with remarkable potential to develop into many different cell types in the body during early life and growth. In addition, in many tissues they serve as a sort of internal repair system, dividing essentially without limit to replenish other cells as long as the person or animal is still alive. There are two primary types of stem cells: embryonic stem cells and non-embryonic "somatic" or "adult" stem cells. Induced pluripotent stem cells (iPSCs) are adult cells that have been genetically reprogrammed to pluripotent stem cells.

Stem cells carry promises for regenerative medicine and cell therapy, but are also changing the drug discovery and development process. Emergence of stem cell technologies provides new opportunities to build innovative cellular models. Stem cell models offer new opportunities to improve the manner in which pharmaceutical companies identify lead candidates and bring new drugs to the market. In spite of promising applications, new competencies surrounding stem cell differentiation and proliferation, induction of pluripotent stem cells and creation of efficacy assays are needed to make successful use of stem cells in drug discovery.

Beyond improved models, pluripotent stem cells technologies are introducing applications that were previously not possible. Currently, human clinical populations are poorly represented in drug development with a lack of genetic heterogeneity in human cellular models and a limited number of human disease models. As a result of induced pluripotent stem cell (iPSC) technology, new cellular models can be created from individuals with a diverse range of drug susceptibilities and resistances, offering the promise of a "clinical trial in a dish" in a field where a personalized medicine approach is becoming increasingly predominant.

Despite these advantages there are still several challenges in using stem cells in drug discovery. The differentiation and reprogramming strategies are not standardized and are often based on growth factors, making protocols expensive, poorly reproducible and limited in terms of scale-up. The pace of stem cell research—for example, a single differentiation or reprogramming experiment currently can take more than a month—is too slow to fit into timelines required by the industry. In addition, before pharmaceutical companies typically will invest in the development of such platforms, further demonstrations of success and potential applications are necessary. And last but not least, stem cell culture and differentiation need to be adapted to the high-throughput environment of drug discovery by developing standardized high-throughput and miniaturized assays for in vitro screening.

SUMMARY

The present disclosure provides compositions and methods employing stem cell-derived amnion tissue. In some embodiments, compositions (e.g., scaffolds and devices) and methods of generating amnion-like tissues from hPSCs are provided. In some embodiments, uses of such cells for research, compound screening and analysis, and therapeutics are provided.

Implantation is a developmental milestone for early human embryos, wherein the blastocyst invades into uterus and develops the amniotic cavity via amniogenesis from epiblasts. However, this process is poorly understood due to limited accessibility to peri-implantation human embryos. Human pluripotent stem cells (hPSCs) provide promising resources for studying early human embryonic development in vitro. The present disclosure demonstrates, using an engineered three dimensional (3D) biomimetic peri-implantation niche, self-organized development of amnion-like tissues from hPSCs, in a manner that recapitulates amniogenesis during implantation. This 3D niche comprises natural biological hydrogel (e.g., Matrigel) or microfabricated artificial matrix to mimic the physicochemical cues within pen-implantation environment. In drastic contrast to biochemically identical two dimensional (2D) culture, it was observed that the bioengineered 3D system successfully induces rapid spontaneous differentiation and self-organization of hPSCs to form 3D lumenal cysts composed of squamous epithelial cells reminiscent of amniotic tissue morphogenesis. These squamous cells express placental tissue markers (e.g. GATA2/3) as well as human amnion-enriched genes, such as PERIOSTIN, showing transcriptional similarity to human amnion cells. The amniogenic development is associated with collective invasion of the lumenal cyst into the 3D matrix, consistent with the invasive phenotype of amnioblasts in vivo. This engineered niche provides the first tool for efficient derivation of human amnion-like tissue and facilitates the study of important but previously inaccessible aspects of early human embryonic development. Furthermore, development of amnion-like tissue from hPSCs is useful for understanding embryo implantation failure and drug screening and therapeutic treatments for embryo implantation failure.

For example, in some embodiments, provided herein is a method for preparing amnion-like tissue, comprising: culturing cells on a solid support coated with a gel matrix, wherein the cells are coated with further gel matrix under conditions such that amnion-like tissue is generated. In some embodiments, the cells are stem cells (e.g., induced pluripotent stem cells or pluripotent stem cells). In some embodiments, the stem cells are human stem cells. In some embodiments, the solid support comprises a plurality of microposts. In some embodiments, the surface is glass or PDMS. In some embodiments, the gel matrix is a natural or synthetic polymer hydrogel (e.g., growth factor basement membrane matrix, collagen or Matrigel). In some embodiments, the amnion-like cells are an asymmetric cyst.

In some embodiments, the cells are generated in a device comprising parallel first, second, and third channels wherein the first and second channels are cell channels comprising a loading reservoir operably linked to the third channel comprising a gel interaction matrix.

Further embodiments provide a composition comprising a plurality of cells produced by the methods described herein.

Other embodiments provide a method for testing a compound, comprising: a) providing a composition described herein b) exposing a test compound to the composition; and c) determining an effect of the test compound on the composition.

Additional embodiments are described herein.

DESCRIPTION OF THE FIGURES

FIG. 3A, Confocal micrographs showing immunostaining of BRACHYURY (BRA; top), SNAIL (middle), and SLUG (bottom) in hPSCs cultured under the indicated conditions and corresponding staining of PS cells derived from hPSCs under 2D culture16 (PS-2D). FIG. 3B, Confocal micrographs showing immunostaining of ECAD (top) and N-CADHERIN (NCAD; bottom) for hPSCs under the indicated culture conditions. FIGS. 3C-D Schemes summarizing the transcriptional control program for canonical EMT (FIG. 3C) and the columnar-to-squamous transition reminiscent of human amnion development (FIG. 3D).

DEFINITIONS

Figure 1:
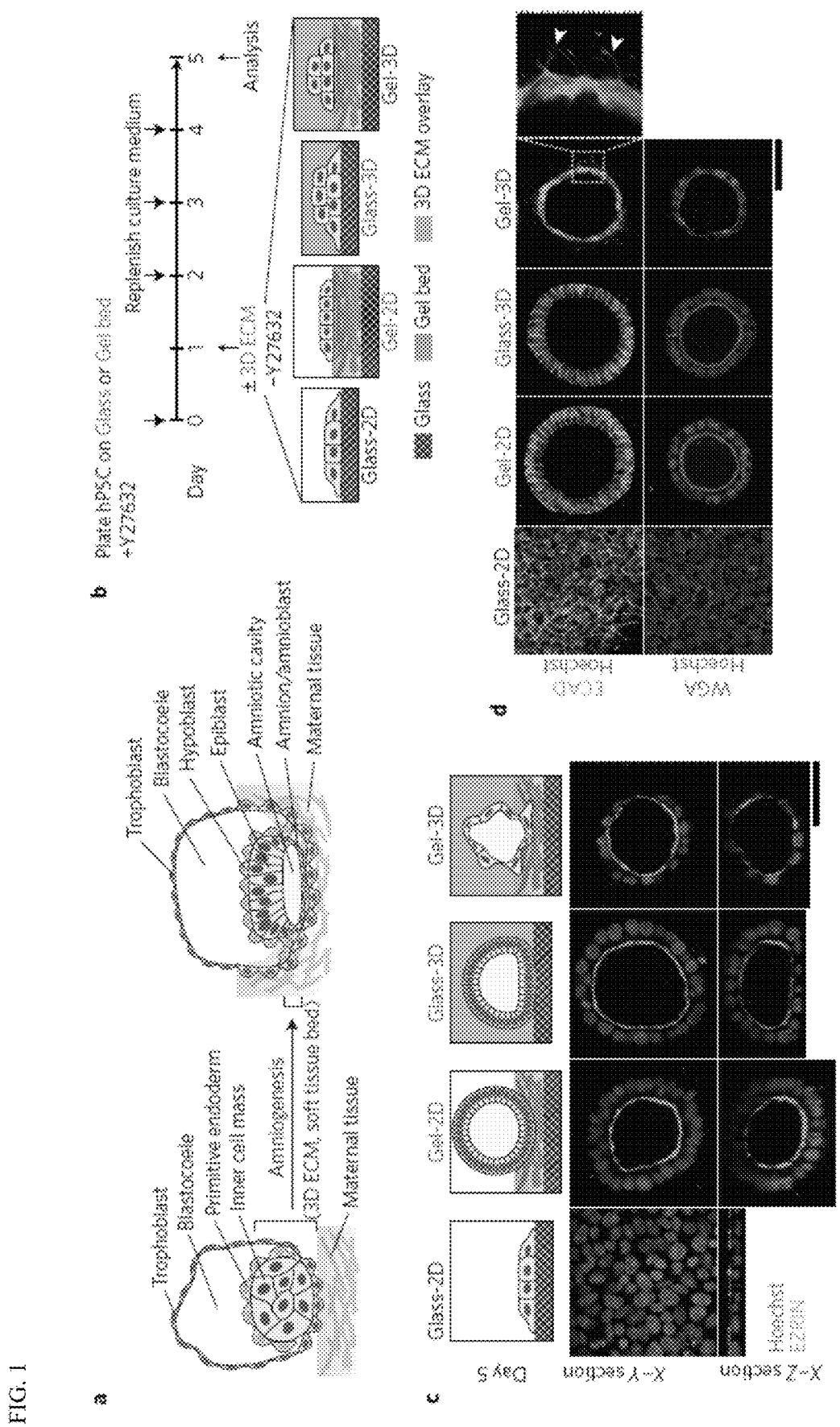
FIG. 1 shows that that hPSCs form squamous cysts with amnion-like morphology in an implantation-like niche. a, Development of amnion/amnioblasts from epiblasts in a peri-implantation human embryo. b, hPSC amniogenesis assay. c, Schematic diagrams showing hPSC morphogenesis under different culture conditions (top). Confocal micrographs showing the X—Y (middle) and X—Z (bottom) sections of the hPSC monolayer and cysts formed in the indicated conditions at day 5. d, Confocal micrographs showing staining of E-CADHERIN (ECAD; top), wheat germ agglutinin (WGA; bottom), and Hoechst (nucleus) in hPSCs cultured under the indicated conditions. e, Box charts showing normalized nucleus dimension (left) and epithelium thickness (right) for hPSC cysts in the indicated conditions (box: 25-75%, bar-in-box: median, and whiskers: 1% and 99%). f, Confocal micrographs showing NANOG (top), OCT4 (middle), and SOX2 (bottom) immunostaining in hPSCs cultured under the indicated conditions. g, Western blot showing protein levels of NANOG, OCT4, SOX2, ECAD and GAPDH in hPSCs cultured under the indicated conditions.
Figure 1:
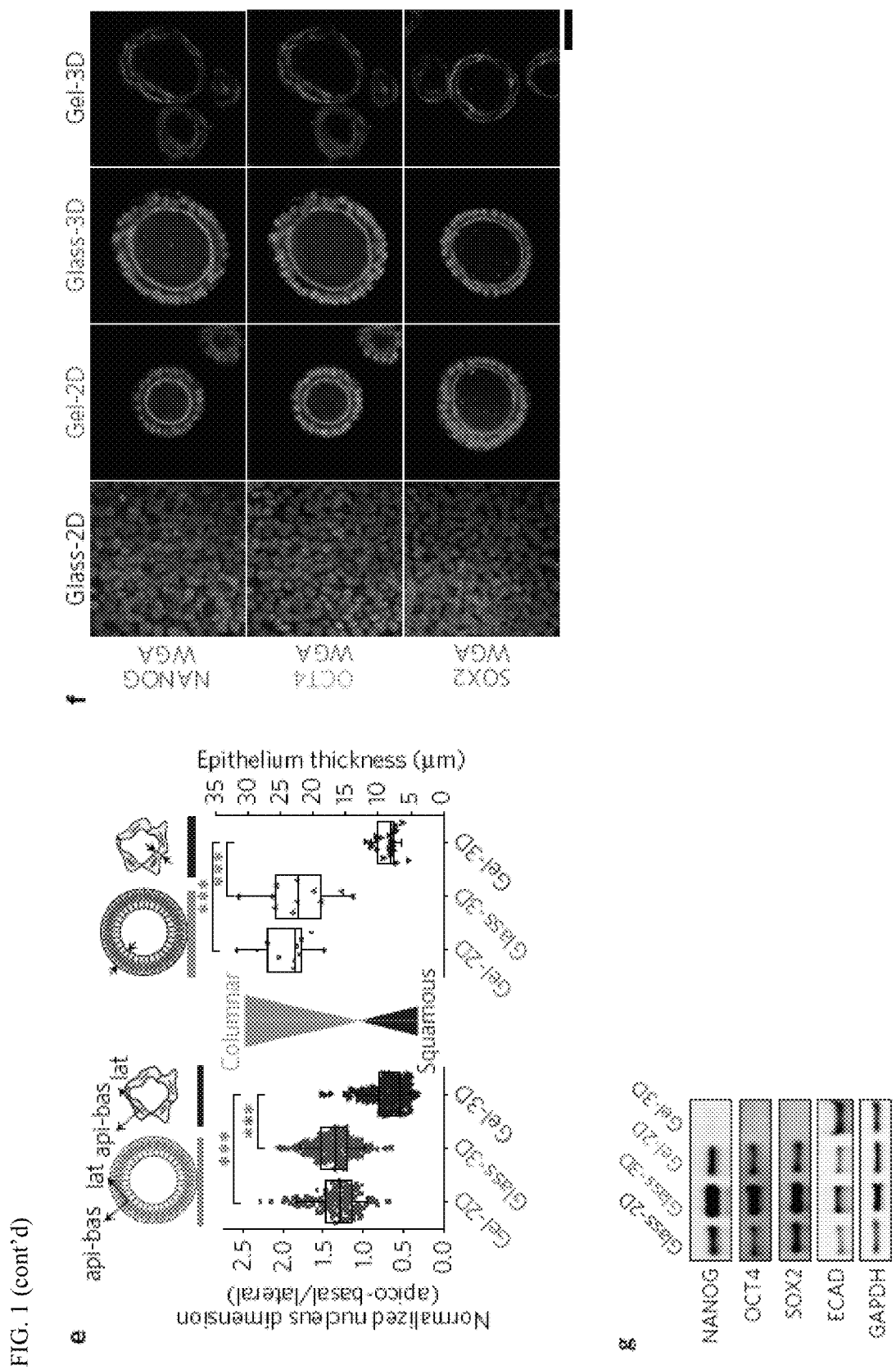

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

The term "administration" and variants thereof (e.g., "administering" a compound) in reference to cells or a compound mean providing the cells or compound or a prodrug of the compound to the individual in need of treatment or prophylaxis. When cells or a compound of the technology or a prodrug thereof is provided in combination with one or more other active agents, "administration" and its variants are each understood to include provision of the compound or prodrug and other agents at the same time or at different times. When the agents of a combination are administered at the same time, they can be administered together in a single composition or they can be administered separately. As used herein, the term "composition" is intended to encompass a product comprising the specified ingredients in the specified amounts, as well as any product that results, directly or indirectly, from combining the specified ingredients in the specified amounts.

By "pharmaceutically acceptable" is meant that the ingredients of the pharmaceutical composition are compatible with each other and not deleterious to the recipient thereof.

The term "subject" as used herein refers to an animal, preferably a mammal, most preferably a human, who has been the object of treatment, observation, or experiment.

The term "effective amount" as used herein means that amount of an agent (e.g., amnion-like tissue) that elicits the biological or medicinal response in a cell, tissue, organ, system, animal, or human that is being sought by a researcher, veterinarian, medical doctor, or other clinician. In some embodiments, the effective amount is a "therapeutically effective amount" for the alleviation of the symptoms of the disease or condition being treated. In some embodiments, the effective amount is a "prophylactically effective amount" for prophylaxis of the symptoms of the disease or condition being prevented.

"Feeder cells" or "feeders" are terms used to describe cells of one type that are co-cultured with cells of another type, to provide an environment in which the cells of the second type can grow. When a cell line spontaneously differentiates in the same culture into multiple cell types, the different cell types are not considered to act as feeder cells for each other within the meaning of this definition, even though they may interact in a supportive fashion. "Without feeder cells" refers to processes whereby cells are cultured without the use of feeder cells.

A cell is said to be "genetically altered" when a polynucleotide has been transferred into the cell by any suitable means of artificial manipulation, or where the cell is a progeny of the originally altered cell that has inherited the polynucleotide. The polynucleotide will often comprise a sequence encoding a protein of interest, which enables the cell to express the protein at an elevated level. The genetic alteration is said to be "inheritable" if progeny of the altered cell have the same alteration.

DETAILED DESCRIPTION

The present disclosure provides compositions and methods employing stem cell-derived amnion tissue. In some embodiments, compositions (e.g., scaffolds and devices) and methods of generating amnion-like tissues from hPSCs are provided. In some embodiments, uses of such cells for research, compound screening and analysis, and therapeutics are provided.

During implantation of a human embryo, amnion cells (amnioblasts) are the first differentiated cell group emerging from an expanding pluripotent epiblast population and give rise to a polarized squamous amniotic epithelium that encloses the amniotic cavity (Dobreva, et al. Int. J. Dev. Biol. 54, 761-777 (2010); Luckett, Am. J. Anat. 144, 149-167 (1975)) (FIG. 1a). Despite its basic and clinical significance, amnion development in humans is poorly understood due to limited studies on peri-implantation human embryos and drastic differences in amniogenesis between human and other commonly used amniote models (Dobreva et al., 2010, supra; Ferner, K. & Mess, A. Respir. Physiol. Neurobiol. 178, 17 3950 (2011). Even with recent progress in developing in vitro systems (Warmflash, A. et al. Nat. Methods 11, 847-854 (2014); Taniguchi, K. et al. Stem Cell Rep. 5, 954962 (2015), including in vitro-cultured human embryos (Deglincerti, A. et al. Nature 533, 251-254 (2016); Shahbazi, M. N. et al. Nat. Cell Biol. 18, 700-708 (2016)), for studying early human embryogenesis, the development of human amnion remains mysterious.

Human pluripotent stem cells (hPSCs), which reside in a developmental state similar to pluripotent epiblasts (O'Leary, T. et al. Nat. Biotechnol. 30, 278-282 (2012); Nakamura, T. et al. Nature 537, 57-62 (2016)) have been successfully utilized for modeling post-gastrulation human embryonic development (Warmflash et al., supra; Lancaster, M. et al. Nature 501, 373-379 (2013)). However, the applicability of hPSCs for modeling peri-implantation, pre-gastrulation developmental events, such as amniogenesis, remains undetermined.

Accordingly, provided herein are scaffolds and devices for generating and utilizing amnion-like tissues.

I. Generation of Amnion-Like Tissue

As described herein, the present disclosure provides compositions and methods for generating and utilizing amnion-like tissue.

Cells

A wide variety of cells and stem cells may be employed with the technology described herein. Such cells include embryonic stem cells and induced pluripotent stem cells, regardless of source. For example, induced pluripotent stem cells may be derived from stem cells or adult somatic cells that have undergone a dedifferentiation process.

Induced pluripotent stem cells may be generated using any known approach. In some embodiments, iPSCs are obtained from adult human cells (e.g., fibroblasts). In some embodiments, modification of transcription factors (e.g., Oct3/4, Sox family members (Sox2, Sox1, Sox3, Sox15, Sox18), Klf Family members (Klf4, Klf2, Klf1, Klf5), Myc family members (c-myc, n-myc, l-myc), Nanog, LIN28, Glis1, etc.) or mimicking their activities is employed to generate iPSCs (using transgenic vector (adenovirus, lentivirus, plasmids, transposons, etc.), inhibitors, delivery of proteins, microRNAs, etc.).

In some embodiments the cells are non-terminally differentiated cells (regardless of pluripotency) or other non-maturated cells.

In some embodiments, cells are screened for propensity to develop teratomas or other tumors (e.g., by identifying genetic lesions associated with a neoplastic potential). Such cells, if identified and undesired, are discarded.

Preparing Tissue

In some embodiments, amnion-like tissues are prepared using a method described herein. For example, in some embodiments, cells are cultured on a solid support coated with a gel matrix and the cells are coated with further gel matrix. The present disclosure is not limited to particular gel matrices. In some embodiments, the gel matrix is a natural or synthetic polymeric hydrogel (e.g., polyethylene glycol (PEG) hydrogels, poly (2-hydroxyethyl methacrylate) (PHEMA) hydrogels, growth factor basement membrane matrix, gelatinous protein mixture secreted by Engelbreth-Holm-Swarm (EHS) mouse sarcoma cells (Matrigel hydrogel), collagen, hyaluronic acid (HA), fibrin, or a combination thereof). In some embodiments, commercially available matrices are utilized (e.g., available from Amsbio Abingdon, UK, Corning, Corning, N.Y., or Trevigen, Inc. (Gaithersburg, Md.) are utilized.

In some embodiments, amnion-like tissues are formed as an asymmetric cyst as shown in FIG. 1.

In some embodiments, devices utilized for preparation of amnion-like tissue comprise a solid support (e.g., PDMS) coated with gel matrix. In some embodiments, the solid support comprises a plurality of microposts. In some embodiments, microposts are 1-100 μm in height (e.g., 1 to 20, 5 to 10, or 8.4 μm). In some embodiments, the microposts are arranged in an array or other configuration. After cells are placed on the matrix, additional matrix is placed on top of the cells.

Figure 13:
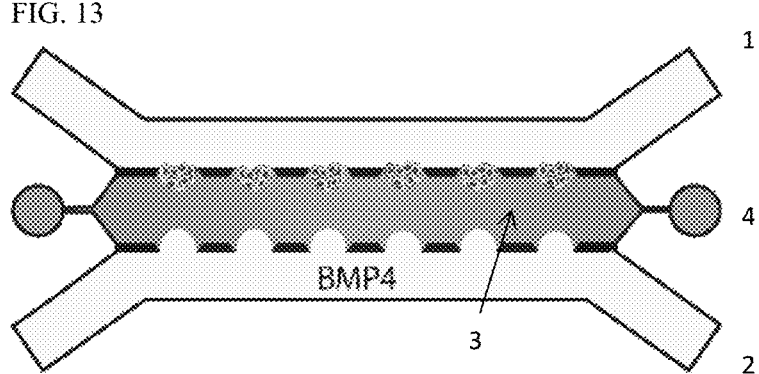
FIG. 13 shows a schematic showing the generation of amnion-like tissue from human pluripotent stem cells on a microfluidic chip.
Figure 14:
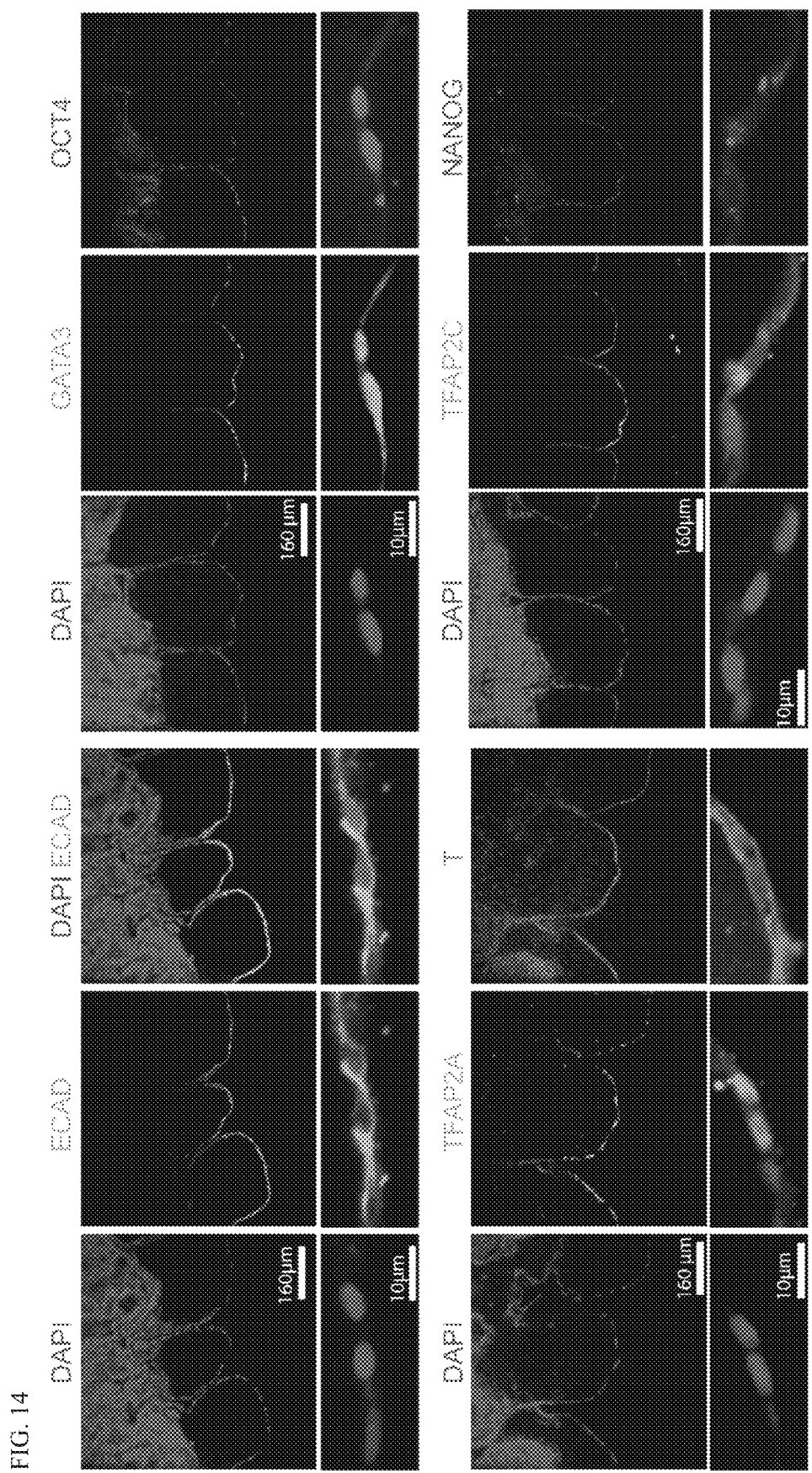
FIG. 14 shows representative confocal micrographs showing the amnion-like tissue developed in microfluidic chips. Zoom-in images are shown for the boxed regions.

In some embodiments, cells are generated in a device comprising parallel first, second, and third channels wherein the first channel 1 and second channel 2 are cell channels comprising a loading reservoir 4 operably linked to the third channel 3 comprising a gel interaction matrix. Exemplary devices are shown in FIG. 13. As shown in FIG. 13, the cell channel 1 (e.g., first channel) is in fluid communication with the cell induction channel 2 (e.g., second channel) via the third channel 3. In some embodiments, E6 medium or other induction medium is added to the induction channel. In some embodiments, Bone morphogenetic protein 4 (BMP4) is added to the induction channel.

II. Uses

Amnion-like tissue provided herein find use in a variety of research, diagnostic, and therapeutic applications.

In some embodiments, cell are utilized in research applications (e.g., study of normal or abnormal amnion development).

In some embodiments, the cells are used for disease modeling and drug development. The quality of the cells and the ability to generate them in a short period of time makes them ideally suited for such research uses, particularly high-throughput analysis. Agents are contacted with the cells to determine the effect of the agent. Cell may also be modified to include a marker and used either in vitro or in vivo as diagnostic compositions to assess properties of the cells in response to changes in the in vitro or in vivo environment.

In some embodiments, cells are used in drug testing or drug toxicity screening applications. For example, in some embodiments, drugs or biological or environmental agents are tested. Indications for drug testing include any compound or biological agent in the pharmaceutical discovery and development stages, or drugs approved by drug regulatory agencies, like the US Federal Drug Agency. All classes of drugs, ethical, over-the-counter and nutraceuticals for any medical indications are known or suspected environmental toxicant may be utilized.

In some embodiments, screening methods are high throughput screening methods.

Embodiments of the present disclosure provide kits comprising the cells described herein. For example, in some embodiments, kits comprise cells (e.g., amnion-like cells or hPSCs) in or on a flexible surface (e.g., multi-well plate or other surface). In some embodiments, kits further comprise reagents for differentiation or use of cells (e.g., buffers, test compounds, controls, etc.).

EXAMPLES

Unless specified otherwise, the following experimental techniques were used in the Examples.

Example 1

Self-Organized Amniogenesis by Human Pluripotent Stem Cells in a Biomimetic Implantation-Like Niche Described herein is a biomimicry approach to engineer a biomaterial-based in vitro hPSC culture system for efficient generation of early human amniotic tissue. Specifically, a biomimetic implantation-like niche for cultured hPSCs was constructed by implementing two major biophysical factors seen in the in vivo amniogenic niche: a three-dimensional (3D) extracellular matrix (ECM) that is provided by the basement membrane surrounding the epiblast during implantation11; and a soft tissue bed provided by the uterine wall and trophoblast to support the developing amnion (FIG. 1a,b). mTeSR1 medium and basement membrane matrix (Geltrex) was used to render the culture permissive for pluripotency maintenance. In this culture system, H9 human embryonic stem cells (hESCs) were plated as single cells at 30,000 cells $cm^2$ onto a thick, soft gel bed of Geltrex (with thickness 100 μm, bulk Young's modulus 900 Pa, coated on a glass coverslip), in mTeSR1 medium supplemented with the ROCK inhibitor Y2763212 (FIG. 1b). At 24 h (day 1), medium containing Y27632 was replaced by fresh mTeSR1 supplemented with 4% (v/v) Geltrex to establish a 3D implantation-like niche (referred to henceforth as the 'Gel-3D' condition). To assess the effect of ECM dimensionality and matrix rigidity, respectively, several modifications of this Gel-3D condition were tested (FIG. 1b). First, the Geltrex supplement was excluded from the medium, with the gel bed retained (referred to henceforth as the 'Gel-2D' condition). Second, the soft gel bed was replaced by a 1% Geltrex-coated glass coverslip (referred to henceforth as the 'Glass-3D' condition). Finally, a standard 2D culture, using a 1% Geltrex-coated glass coverslip (referred to henceforth as the 'Glass-2D' condition), was examined as a control that maintains hPSC self-renewal. Culture medium was replenished daily. Analyses were performed at day 5 unless otherwise noted (FIG. 1b).

In the Glass-2D condition, apico-basally polarized hESC colonies were observed at day 5. Strikingly, in the Gel-2D, Glass-3D and Gel-3D conditions, hESCs formed 3D cysts with EZRINC apical surfaces facing inward, reflecting the intrinsic luminogenic property of hESCs (Taniguchi et al., supra; Shahbazi et al., supra). In both Gel-2D and Glass-3D, >90% of lumenal cysts are made of tall, columnar E-CAD-HERINC (ECADC) epithelial cells with apico-basally elongated nuclei and thick epithelium (FIG. 1c,e). In distinct contrast, >90% of cysts formed in Gel-3D show a squamous epithelial morphology featuring flattened, laterally elongated cell nuclei and reduced epithelium thickness, as well as unique ECADC protrusions extending from basal surfaces (FIG. 1c,e). Notably, all 3D columnar epithelial cysts that formed in the Gel-2D and Glass-3D conditions express the pluripotency markers NANOG, OCT4 and SOX213, consistent with the association between columnar epithelial morphology and pluripotent epiblast in vivo2,6,9 (FIG. 1f,g). However, in squamous cysts that formed in Gel-3D, expression of NANOG, 5 OCT4 and SOX2 protein is lost, indicating that they are composed of a differentiated cell type (FIG. 1f,g). qRT-PCR analysis shows reduction in messenger RNA expression for NANOG and SOX2, but not OCT4 (also known as POU5F1), in Gel-3D, indicating a blunted transcriptional regulation of OCT4.

Despite loss of pluripotency markers, the squamous cyst maintains an epithelial phenotype, retaining expression of ECAD/CDH1 and CLDN614 (FIG. 1d,g). This spontaneously differentiated squamous epithelial cystic tissue is morphologically reminiscent of the developing amnion in pen-implantation human embryos (Dobreva et al., supra; Luckett et al., supra). The development of squamous cysts is characterized by concurrent changes in morphology and cell fate. From days 2-4, the majority of cysts in Gel-3D transitioned from columnar to squamous morphology and lose NANOG and OCT4 expression. Self-organized development of squamous cysts was also observed in two additional hESC lines (UM63-1 and H7) and an hiPSC line (1196a) cultured in Gel-3D, but not under the Glass-2D, Gel-2D or Glass-3D conditions. Thus, uniquely among all conditions examined, the implantation-like Gel-3D biophysical niche is both necessary and sufficient for efficiently inducing self-organized development of hPSCs to a cystic epithelial tissue with amnion-like squamous morphology, under biochemical conditions that permit hPSC self-renewal. Furthermore, the development of squamous cysts in Gel-3D is inhibited as the thickness of the gel bed is decreased to 60 μm or 20 μm, a modulation known to increase apparent substrate rigidity. Together, these findings support the notion that the mechanical rigidity and the 3D dimensionality of the ECM are integrated to trigger hPSC differentiation to an amnion-like tissue.

Figure 2:
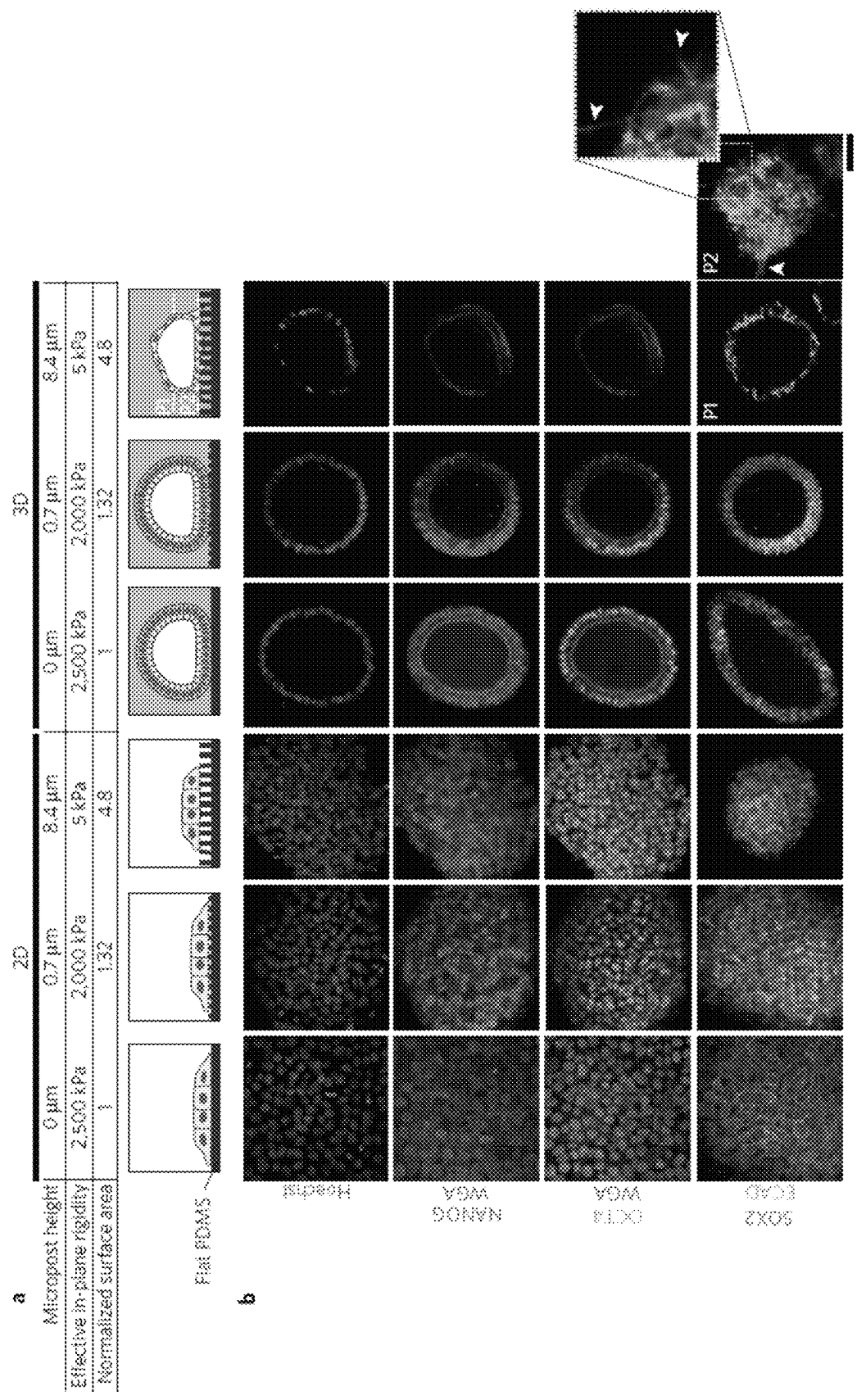
FIG. 2 shows development of squamous cysts from hPSCs on a synthetic, soft artificial matrix. a, Specifics and schematic diagrams of culture conditions using artificial matrices made of PDMS microposts of different post heights. b, Confocal micrographs showing staining of NANOG, OCT4, WGA, ECAD, and SOX2 for hPSCs cultured in the indicated conditions.

To further confirm the physical niche dependency of hPSC morphogenic cyto differentiation, an artificial matrix, made of a regular array of elastomeric polydimethylsiloxane (PDMS) microposts whose height can be precisely modulated to control substrate rigidity and surface area, was utilized (FIG. 2a). Consistently, development of squamous cysts occurred only in hPSCs cultured on 8.4-μm-tall microposts (a soft matrix), but not on 0.7-μm-tall microposts or on flat PDMS surfaces (rigid matrices), even though all included a 3D Geltrex overlay (FIG. 2b). Interestingly, hPSCs 26 cultured on soft 8.4-μm-tall microposts in 2D (that is, without the Geltrex overlay) did not form cysts (FIG. 2), in contrast to columnar 28 cysts formed in Gel-2D (FIG. 1c).

Figure 3A:
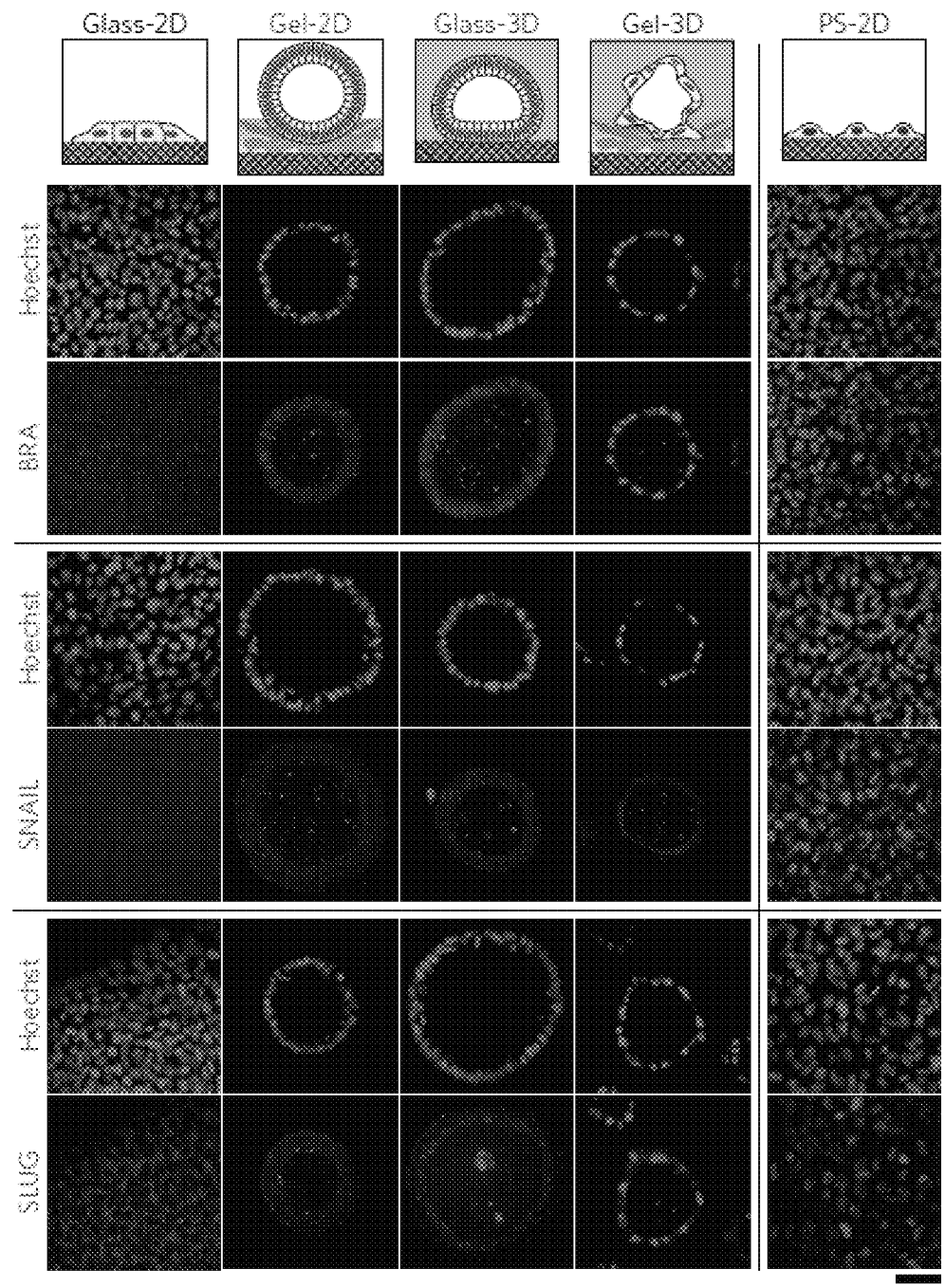
FIGS. 3A-D show squamous cyst development is transcriptionally distinct from canonical EMT or primitive streak.
Figure 3B:
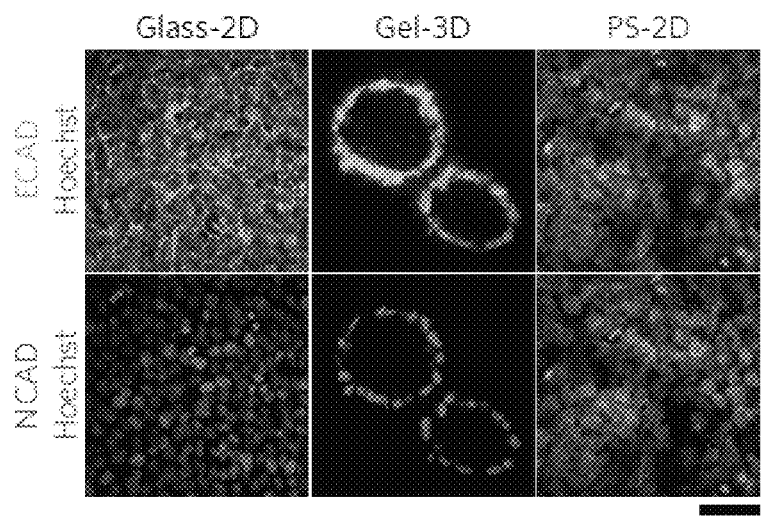
Figure 3C:
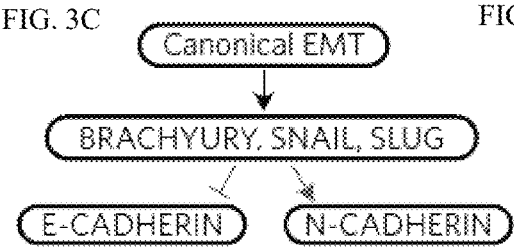
Figure 3D:
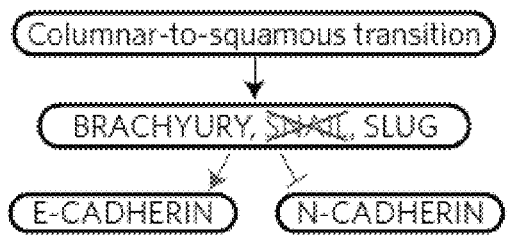

The molecular signature of hPSC-derived squamous cysts was compared with other embryonic and extra-embryonic lineages possibly existing in a peri-implantation embryo, including primitive streak (PS), neuroectoderm, primitive endoderm (PE)/hypoblast, trophectoderm (TE)/trophoblast, primordial germ cells (PGCs), and amnion. Primitive streak development is associated with an epithelial-to-mesenchymal transition (EMT) accompanied by upregulation of transcription factors including BRACHYURY (BRA), SNAIL and SLUG (Thiery, et al. Cell 139, 871-890 (2009)). Indeed, basal protrusions observed in squamous cysts (FIG. 1d) indicates the possible involvement of EMT. Compared with control hPSCs in Glass-2D, upregulation of BRA/BRA and SLUG/SNAI2, but not SNAIL/SNAI1, were observed in squamous cysts in Gel-3D; no upregulation of these transcription factors was seen in the Gel-2D or Glass-3D conditions (FIG. 3a). In contrast, hPSC-derived PS cells (via a 2D culture protocol (Mendjan, S. et al. Cell Stem Cell 15, 310-325 (2014); referred to henceforth as PS-2D cells) showed upregulation of BRA/BRA, SNAIL/SNAI1 and SLUG/SNAI2 (FIG. 3a). PS-2D cells also showed a decrease in ECAD/CDH1 and loss of ECAD organization, accompanied by increased NCAD/CDH2; none of these changes were seen in squamous cysts in Gel-3D (FIG. 3b). These data indicate that while PS-52 2D cells exhibit molecular signatures of canonical EMT (FIG. 3c), squamous cyst development activates a unique subset of EMT-related transcription factors, notably without SNAIL, and elicits a columnar-to-squamous epithelium transition with ECAD/NCAD regulation distinct from that observed in canonical EMT and PS lineage differentiation (FIG. 3d). FOXA2/

Figure 4A:
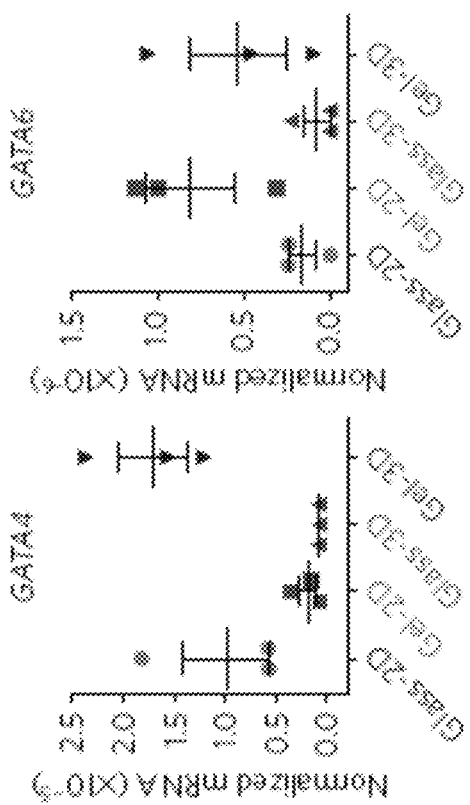
FIG. 4 shows molecular characterization and identification of the squamous, hPSC-derived amnion-like tissue. a-e, qRT-PCR analysis of known markers: primitive endoderm/ hypoblast markers GATA4 and GATA6 (a); trophectoderm and trophoblast markers GATA2, GATA3, CDX2 and TP63 (b); first-trimester human amnion markers ITGB6, VTCN1, GABRP, MUC16, HAND1, POSTN, TFAP2A, TFAP2B, KRT17 and KRT18 (c-e). f, Heat map showing expression levels of 108 putative pluripotency genes, the 50 most upregulated genes (UP-50), and the 50 most downregulated genes (DOWN-50) in hPSC-amnion derived in Gel-3D relative to hPSC colonies in Glass-2D. nD3 biological replicates. g, Hierarchical clustering of ~4,000 prospective hPSC-amnion-enriched genes among hPSC colonies (Glass-2D), hPSC-amnion (Gel-3D), and published fetal extra-embryonic tissues including week-9 amnion and umbilical cord (Amn9, Umb9), week-16 amnion and chorion (Amn16, Chor16), week-18 amnion (Amn18), and week-22 amnion and chorion (Amn22, Chor22).
Figure 4B:
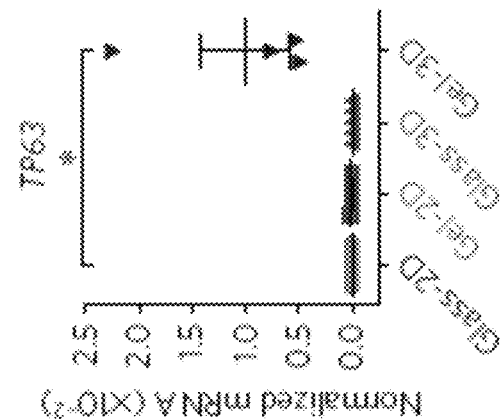
Figure 4B:
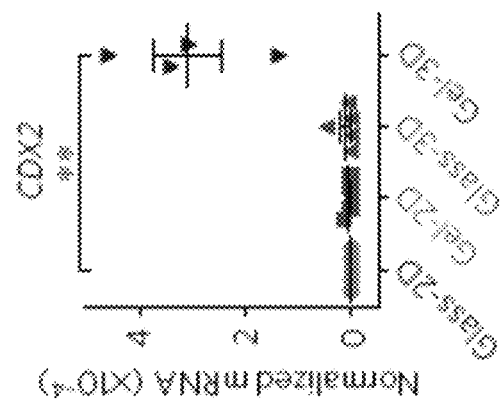
Figure 4B:
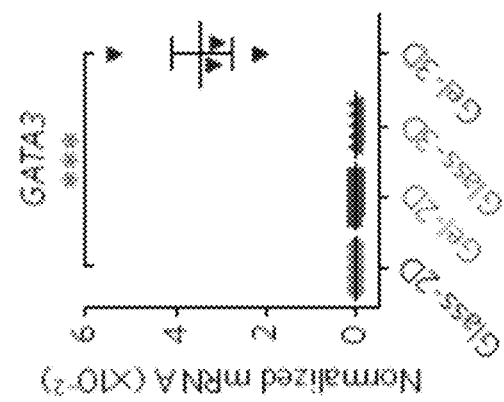
Figure 4B:
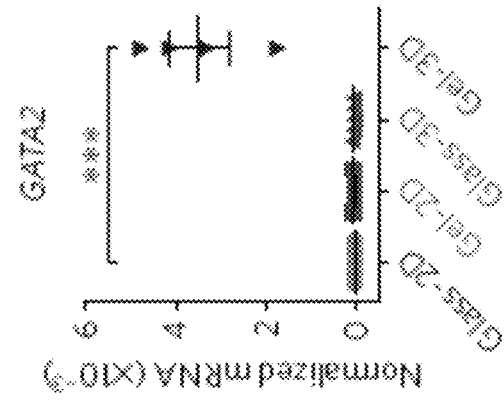

FOXA2, a PS/endoderm marker, was undetectable in squamous cysts, further excluding the PS lineage. Absence of SOX2-a marker of human neuroepithelium in squamous cysts (FIGS. 1f,g and 2) excludes the neuroectodermal lineage. PE/hypoblastmarkers GATA4 and GATA6 were not unregulated in squamous cysts, 6 compared with hPSCs, excluding the PE lineage (FIG. 4a). A recent publication shows that in cynomolgus monkey embryos, PGCs are NANOG+/OCT4+/SOX17+ and emigrate from the amnion by canonical EMT (Sasaki, K. et al. Dev. Cell 39, 169 (2016)). However, none of NANOG/OCT4/SOX17, nor canonical EMT, was detected in squamous cysts (FIGS. 1f,g). Therefore, the squamous cysts do not appear to match the characteristics of PGCs. Interestingly, several TE/trophoblast markers, GATA2, GATA3, CDX2 and TP63 (Deglincerti et al., supra; Li, et al. Development 140, 3965-3976 (2013)) were highly upregulated in squamous cysts compared with hPSC colonies and columnar cysts (FIG. 4b). However, other known trophoblast markers KRT7, CGA and HLA-G (Li et al., supra; Lee et al., Stem Cell Rep. 6, 257-272 (2016)) were not upregulated in squamous cysts. The squamous cysts showed heterogeneous staining of CDX2 and GATA3, which co-localize with BRA, combinations not seen in hPSC-derived trophoblasts (Li et al., supra). SSEA-4, a surface antigen associated with the inner cell mass, but not TE (Henderson, J. K. et al. Stem Cells 20, 329-337 (2002)), is also retained in squamous cysts. Other studies have reported GATA2, GATA3 (Li et al., supra; Roost, M. S. et al. Stem Cell Rep. 4, 1112-1124 (2015) and SSEA-4 (Dobreva et al., supra; Miki, T. & Strom, S. C. Stem Cell Rev. 2, 133-141 (2006) expression in human amnion. Together, these results contradict known molecular features of trophoblasts, and support that the hPSC-derived squamous cystic tissue resembles early human amnion.

Figure 4C:
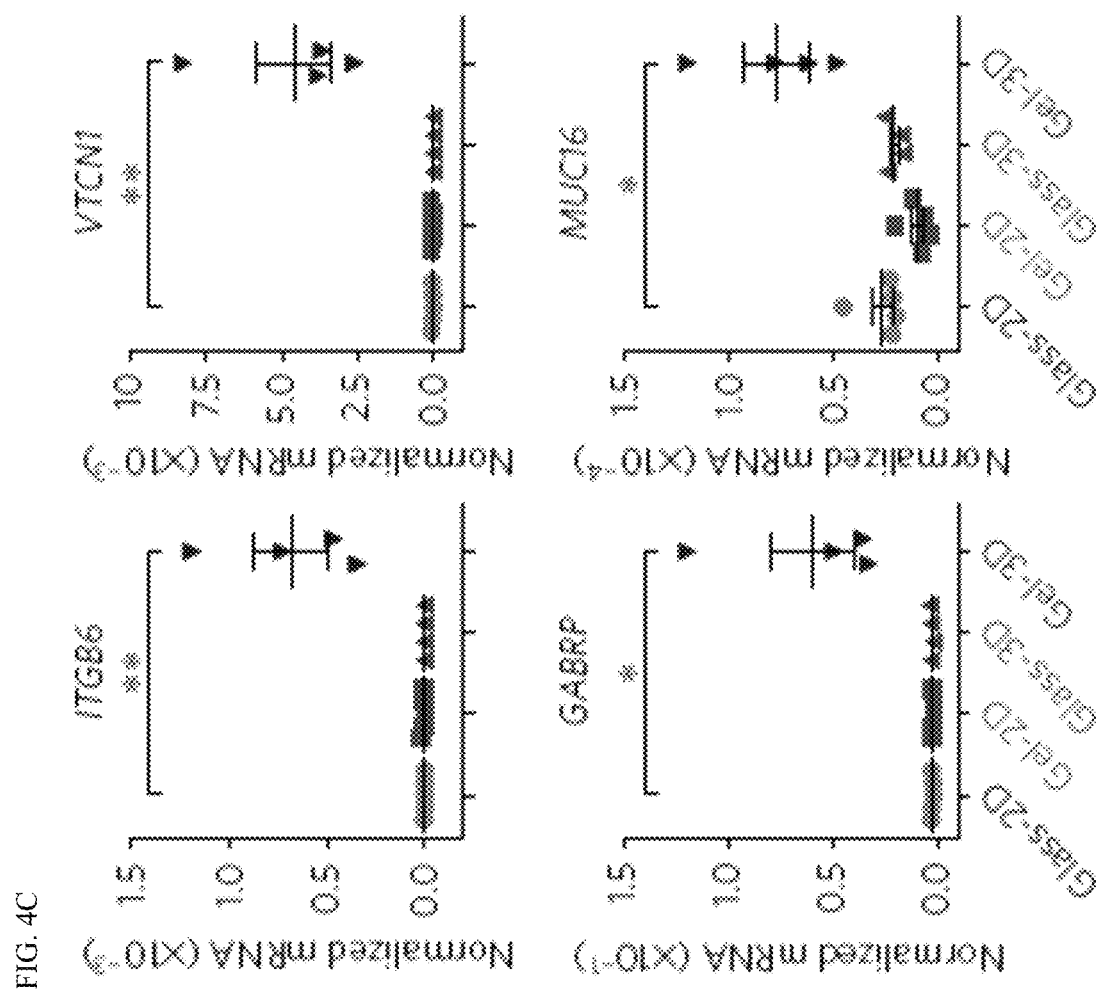
Figures 4D, 4E:
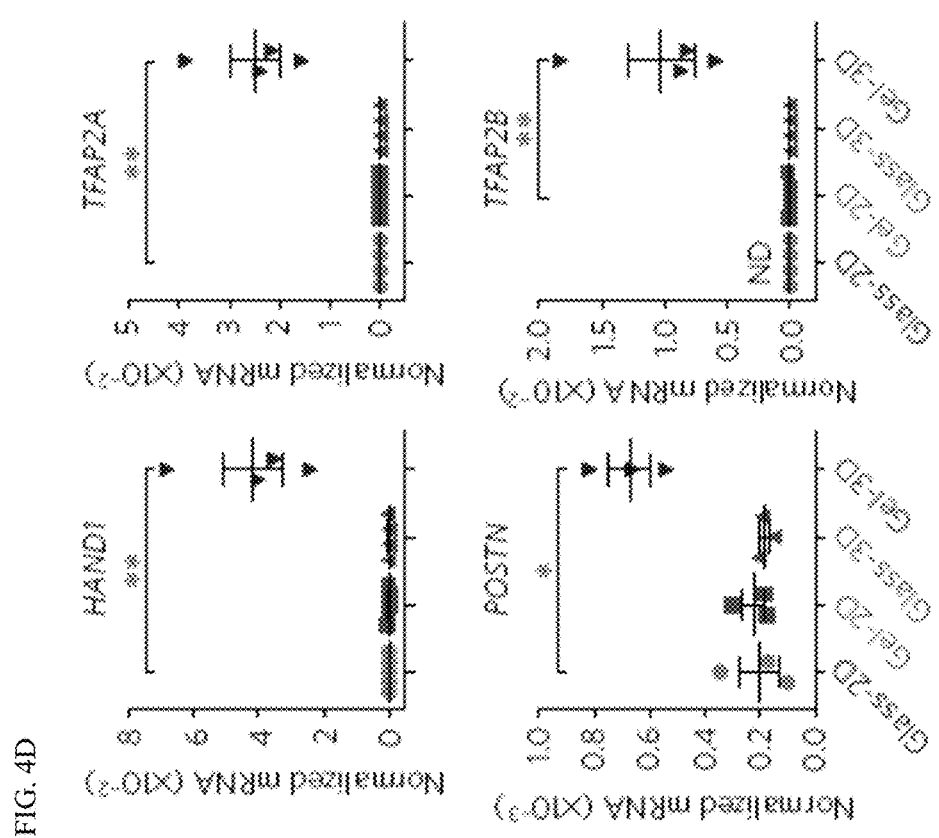

Consistently, mRNA expression of a set of key fate-identifying genes recently reported for first-trimester human amnion-ITGB6, VTCN1, GABRP and MUC16 (Roost et al., supra) are all significantly upregulated in squamous cysts compared with control hPSCs (FIG. 4c). Additionally, squamous cysts exhibit upregulated expression of HAND1, POSTN, TFAP2A and TFAP2B (FIG. 4d); HAND1, POSTN and TFAP2A are markers for early mouse (Mallon, B. S. et al. Stem Cell Res. 10, 57-66 (2013)) amnion (Dobreva, M. P. et al. Stem Cells Int. 2012, 987185 (2012)), and POSTN, TFAP2A and TFAP2B are reported first-trimester human amnion markers (Roost et al., supra; Dobreva et al. 2012, supra; Slieker, R. C. et al. PLoS Genet. 11, e1005583 (2015)). The squamous cysts also show upregulation of KRT17 and KRT18 (FIG. 4e), which are observed in week-10 human amnion (Regauer, et al. J. Cell Biol. 100, 997-1009 (1985)). Together, these data demonstrate that, among all of the candidate lineages, the hPSC-derived squamous cysts exhibit a molecular signature most closely matching known aspects of human amnion at the first trimester (for example, week 9-10), the earliest stage reported so far in the literature.

Figure 4F:
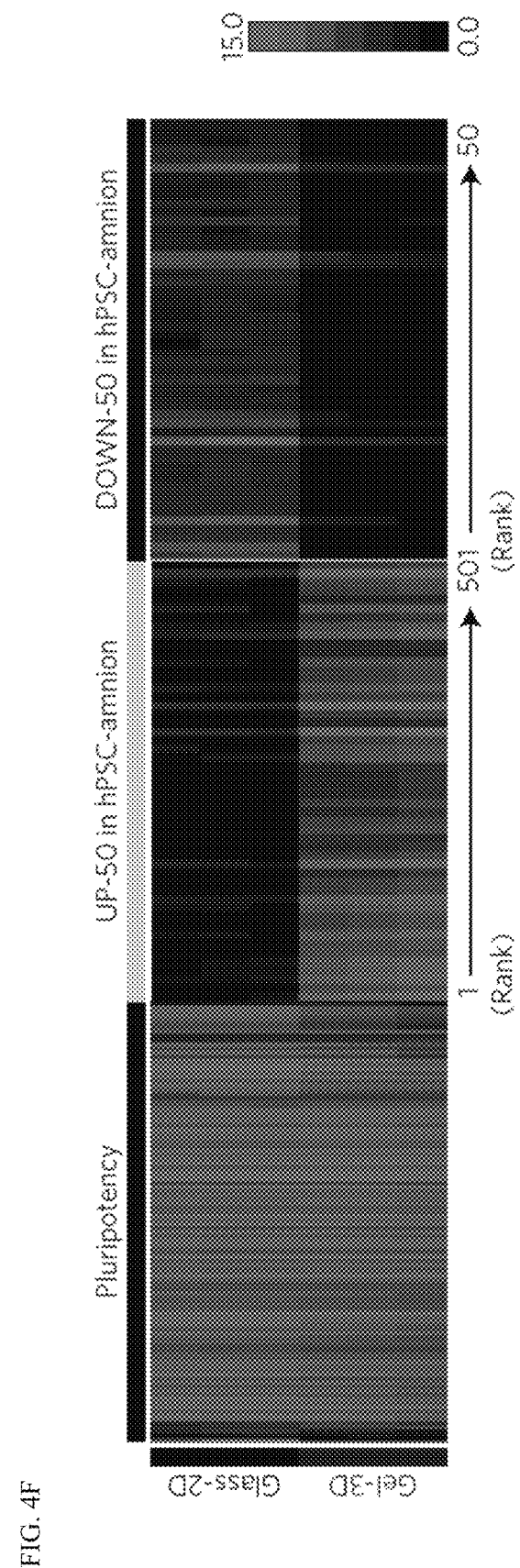

To establish the transcriptome of the hPSC-derived amnion-like tissue (referred to henceforth as hPSC-amnion), RNA-sequencing (RNA-seq) was performed. Although the transcriptome of hPSC-amnion differs substantially from that of control hPSCs, expression levels of a cohort of putative pluripotency genes are remarkably similar in both; only CUZD1 and CCL26 are substantially downregulated in hPSC-amnion compared with control hPSCs (FIG. 4f). This observation shows that hPSC-amnion develops with only slight downregulation of the transcriptional circuitry maintaining pluripotency, consistent with the emergence of amnion from expanding pluripotent epiblasts in a self-renewal-permissive environment in vivo and here in vitro.

4,000 genes with higher expression in hPSC-amnion than in hPSCs or in previously examined fetal extra-embryonic tissues, including amnion, chorion and umbilical cord (GEO access number GSE66302) (FIG. 4g), were subjected to hierarchical clustering. This revealed a gene set uniquely enriched in hPSC-amnion and relatively depleted in hPSCs and other extra-embryonic tissues (FIG. 4g), reflecting the fact that the pen-implantation stage represented by hPSC-amnion is developmentally earlier than previously examined amnion (Roost et al., supra; Slieker et al., supra; Pereira, P. N. et al. BMC Dev. Biol. 11, 48 (2011)) samples (Li et al., supra; Roost et al., supra; Slieker et al., supra). Genes enriched in hPSC-amnion were compared with recently reported single-cell transcriptomes of 197 non-amniotic cells obtained from post-implantation monkey embryos (Nakamura et al., supra). This analysis did not reveal any monkey cell that either displays transcriptomic similarity to hPSC-amnion or is double-positive for the hPSC-amnion markers ITGB6 and VTCN1, supporting that hPSC-amnion represents a distinct lineage.

Gene ontology (GO) functional annotation clustering was performed for genes enriched in hPSC-amnion. GO terms for genes enriched in 9-week human amnion as well as human chorion and placenta were similarly clustered. The three most enriched annotation clusters in hPSC-amnion were transcription factors, primarily those of the homeobox classes. HOX genes comprised the highest ranked cluster in 9-week amnion as well.

Figure 4G:
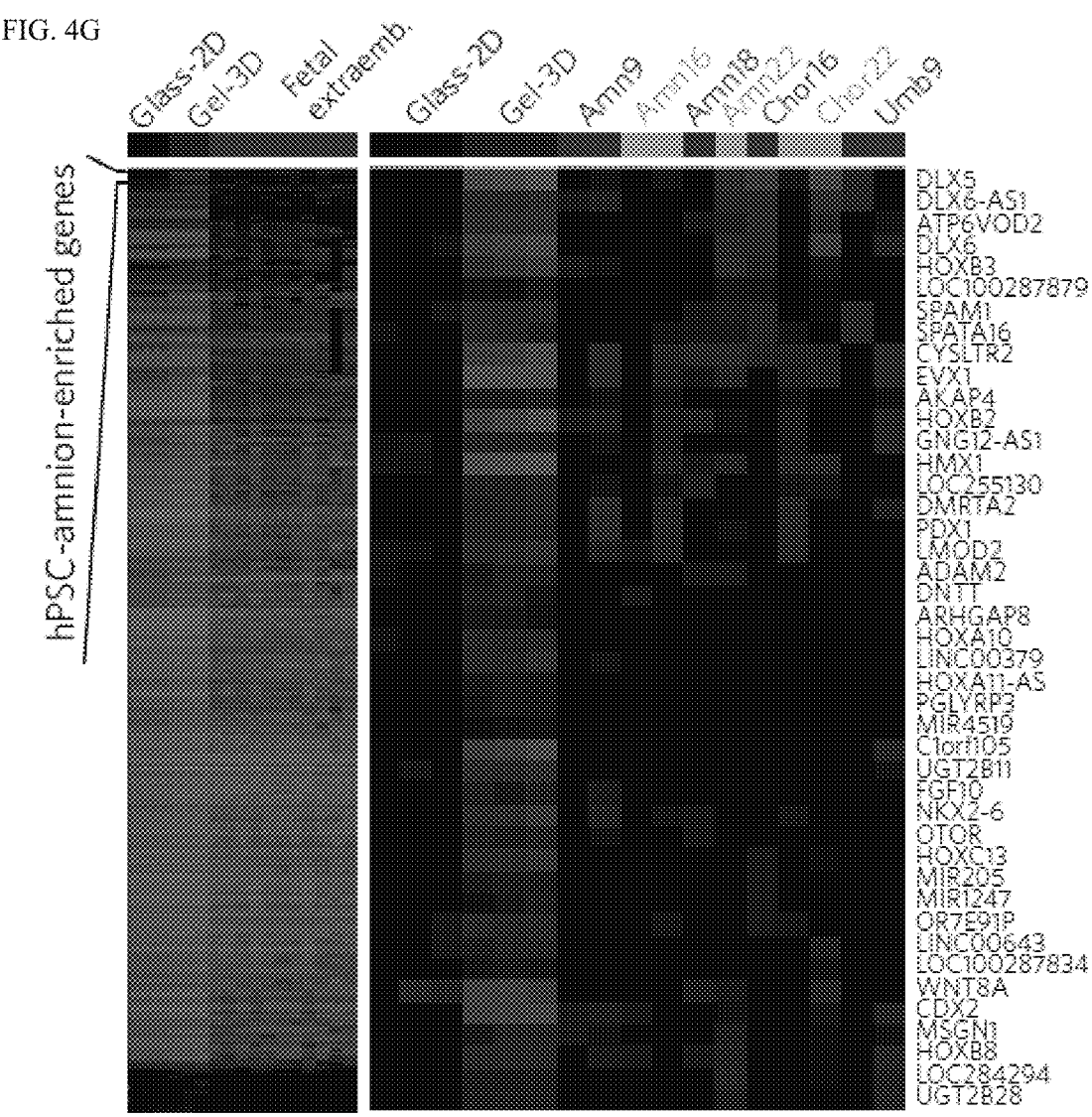
Figure 5C:
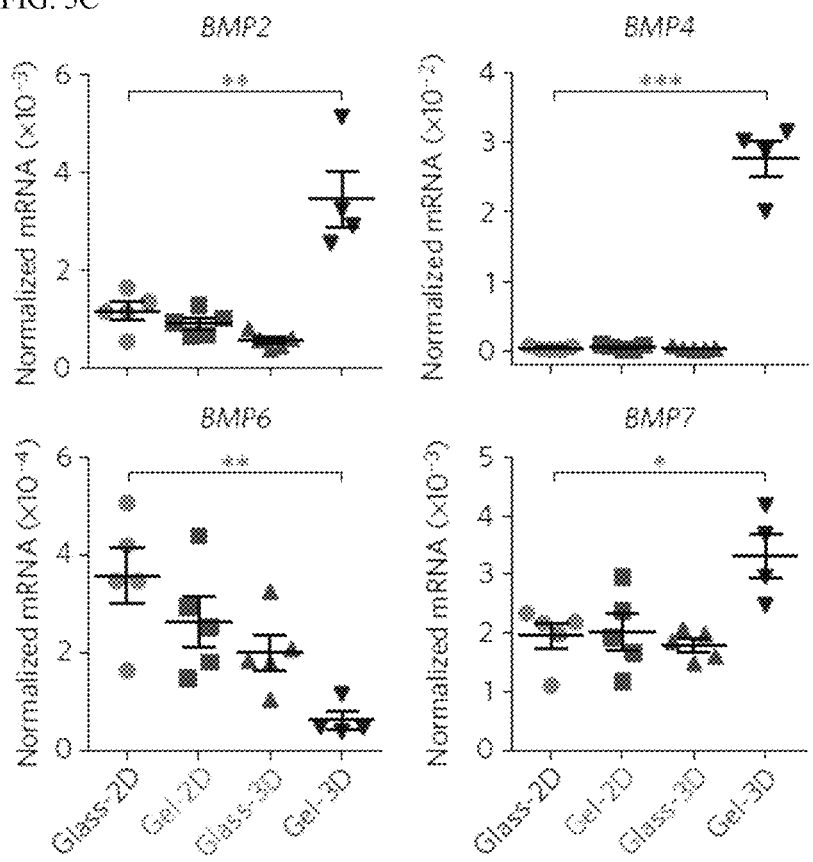
FIG. 5 shows endogenously activated BMP-SMAD signaling is required for the development of hPSC-amnion. a, Confocal micrographs showing immunostaining of phosphorylated SMAD1/5 (pSMAD1/5) in hPSCs cultured under the indicated conditions. Hoechst counterstains nuclei. nD2 independent experiments. b, Western blot showing protein levels of pSMAD1/5, SMAD1/5/8 and GAPDH for hPSCs cultured under the indicated conditions. nD3 independent experiments. c, qRT-PCR analysis of BMP2, BMP4, BMP6 and BMP7 for hPSCs cultured under the indicated conditions. d, Confocal micrographs showing immunostaining of NANOG (top), OCT4 (middle), SOX2 (bottom), pan-cell membrane marker WGA (top and middle), and basolateral membrane marker ECAD (bottom), in hPSC-derived epithelial cysts under the Glass-3D and Gel-3D conditions with or without supplementation of BMP inhibitor LDN193189 (LDN) as indicated.

Among genes enriched in hPSC-amnion were several potential BMP targets including DLX5/6 and EVX1 (FIG. 4g). Gene set enrichment analysis also revealed enrichment of genes related to the ALK pathway, which is associated with BMP signalling, in hPSC-amnion compared with hPSCs. Indeed, prominent nuclear staining and upregulated protein level of phosphorylated SMAD1/5 (pSMAD1/5), a downstream target of BMP-SMAD signalling, was observed in hPSC-amnion, but not in other conditions (FIG. 5a,b). It indicates that BMP-SMAD signalling is activated during hPSC-amnion development, consistent with findings in early mouse and primate embryos (Sasaki, K. et al. Dev. Cell 39, 169 (2016); Henderson et al., supra; Dobreva et al., 2012, supra; Pereira et al., supra). Consistently, both RNA-seq and qRT-PCR analysis (FIG. 5c) show upregulated BMP2/4/7 in hPSC-amnion. Western blotting further confirms increased BMP4 protein level in hPSC-amnion, showing endogenously activated BMP production during the development of hPSC-amnion.

Figure 5D:
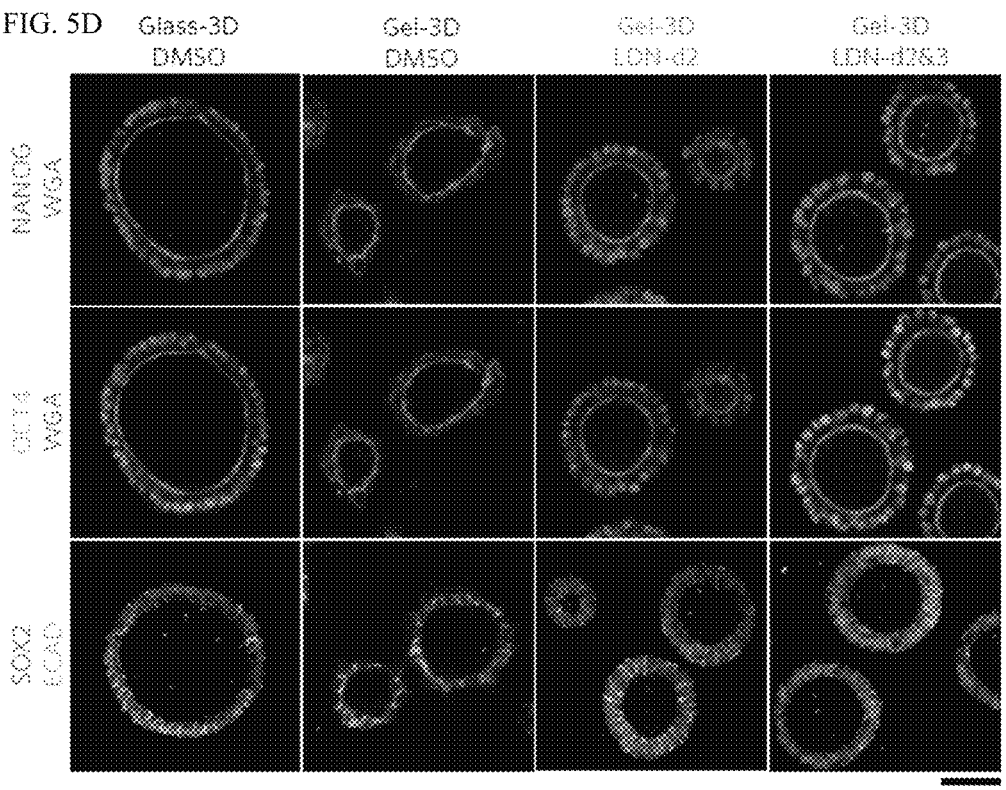

To examine whether BMP-SMAD signalling is required for hPSC-amnion development, hPSCs cultured in Gel-3D were treated with a small-molecule inhibitor LDN193189 (LDN), which inhibits ALK2/3 receptors that bind to BMP2/4/7. Treatments with LDN (on day 2 alone or on both days 2 and 3) inhibited hPSC-amnion development (FIG. 5d). The development of hPSC-amnion is also inhibited by treatment with NOGGIN, a protein that antagonizes BMP2/4/7. These results implicate the requirement of BMP-SMAD signalling for hPSC-amnion development.

This example describes a biomimetic implantation-like niche for hPSCs to model human amniogenesis, a key developmental step previously not accessible to study. It was demonstrated that amniotic development by hPSCs is a self-organizing process that occurs in the absence of biochemical inductive cues from a maternal or extra-embryonic source. Rather, physical signals from the implantation-like niche are necessary and sufficient to trigger the development of amnion-like tissue in a BMP-dependent manner. In addition to advancing fundamental understanding of human amnion development and expanding the application of hPSCs to model pen-implantation human embryogenesis, this efficient hPSC-based 3D amniogenic system finds use in high-throughput screening assays to predict human reproductive success, examine the effect of toxins on amniotic development, and provide a therapeutic strategy for in utero treatment of amniotic tears.

Example 2

An In Vitro Model for Human Amniotic Sac Development

During human embryo implantation, the embryonic inner cell mass gives rise to the amniotic sac—an asymmetrically patterned epithelial cyst that encloses the amniotic cavity with squamous amnion at one pole and columnar epiblast at the other (FIG. 6a) (Luckett et al., supra). Historically, human amniotic sac development is mysterious due to the scarcity and restricted availability of early embryo specimens. Despite recent progress in culturing human embryos in vitro (Deglincerti et al, supra; Shahbazi et al., supra), amniotic sac development in human remains poorly accessible for study.

Human pluripotent stem cells (hPSCs), which share similarity with the epiblast in human Embryo (O'Leary et al., supra; Nakamura et al., supra; Yan, L., et al. Nat. Struct. Mol. Biol. 20, 1131-1139 (2013)), have been widely utilized for modeling post-gastrulation human development in vitro (Warmflash et al, supra; Lancaster et al., supra; Takasato, M., et al. Nature 526, 564-568 (2015); Nakano, T., et al. Cell Stem Cell 10, 771-785 (2012)). The application of hPSCs was expanded to model pen-implantation amniogenesis by using a biomimetic implantation-like three dimensional (3D) culture system (Example 1). It was demonstrated that this culture system can efficiently induce the development of squamous, human amnion-like cysts from hPSCs. On day 5, a small population of asymmetric cysts was observed in this 3D culture system (FIG. 6b), showing concomitant development of a structure more complex than the simple squamous amnion.

Figure 6A:
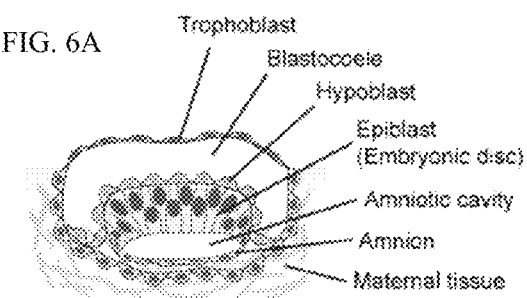
FIG. 6 shows self-organized, hPSC-derived amniotic sac embryoids (ASEs) to model preimplantation human amniotic sac development. (a) Cartoon of an implanting human embryo. (b) Schematic of the 3D culture system for generating ASEs from hPSCs. (c) Confocal micrographs showing an ASE on day 5, stained with indicated markers. Scale bar, 50 µm. (d) Carnegie stage (CS) 5a-2, 5b, and 5c human embryo sections, showing prospective and definitive amnion (Am.) and epiblast (Epi.). Phase contrast image shows the ASE. (f) Confocal micrographs showing an ASE on day 5, stained with indicated markers. Scale bar, 50 µm. (g) Confocal micrographs showing self-organized development of ASEs from day 2-5. (h) Cartoon showing the time course of ASE development in vitro, compared with human amniotic sac development in vivo.
Figure 6B:
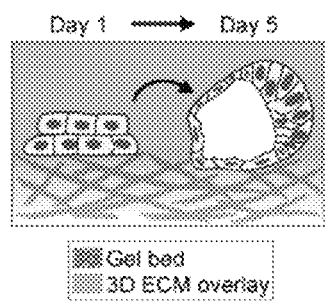
Figure 6C:
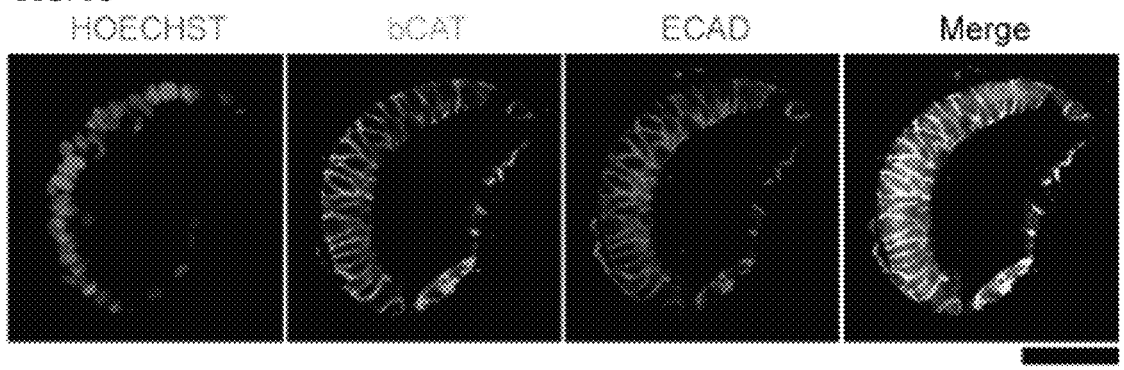
Figure 6D:
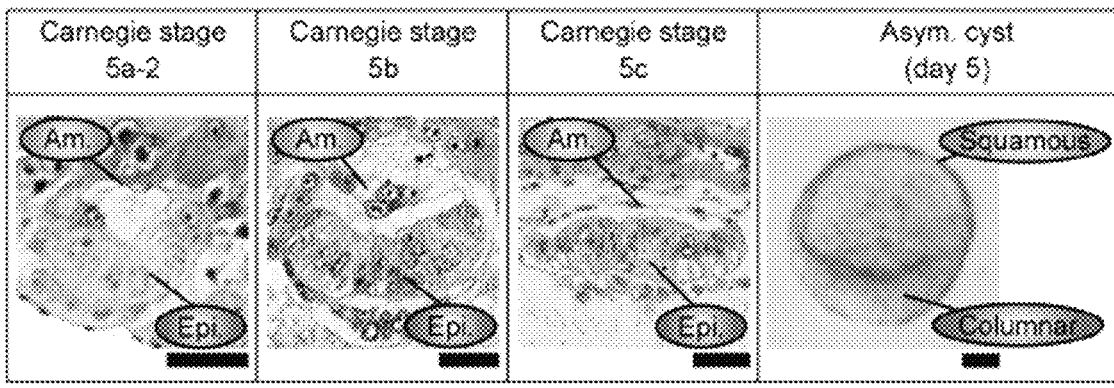

These asymmetric cysts are E-CADHERIN+/β-CATENIN+ (ECAD+/bCAT+) epithelial sacs composed of tall, columnar cells on one side, and flattened, squamous cells on the other (FIG. 6c). They are apico-basally polarized with EZRIN+, WGA-enriched apical surfaces facing inward. These asymmetric cysts morphologically resemble the bipolar amnion-epiblast patterning within the amniotic sac in human embryos at Carnegie stages 5a-2, 5b, and 5c, on day past fertilization (d.p.f) 8, 9, and 12, respectively (FIG. 6d). Notably, such asymmetric cyst frequently forms with the squamous side oriented towards the thick gel matrix underneath.

Figure 6E:
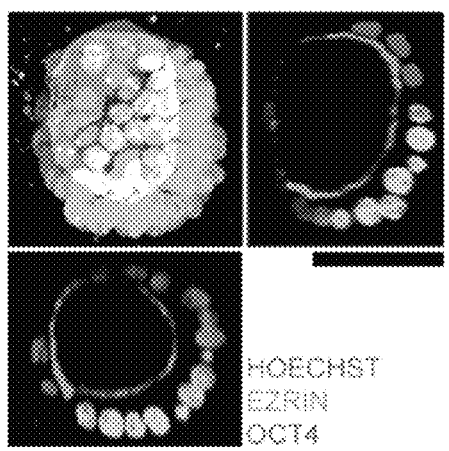
Figure 6F:
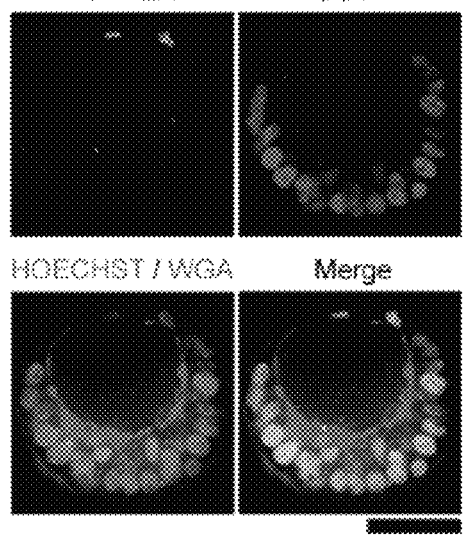

The columnar side of the asymmetric cyst is composed of cells that prominently retain pluripotency marker OCT4 (also known as POU5F1), which is lost in the squamous cells (FIG. 6e). Co-staining OCT4 with other pluripotency markers—NANOG and SOX2, respectively—confirms that the columnar side of the asymmetric cyst is generally composed of undifferentiated, epiblast-like hPSCs, resembling the embryonic disc lining at one pole of the amniotic sac (FIG. 6a). Consistent with this contention, OCT4/NANOG co-staining was seen exclusively in the embryonic disc of cynomolgus monkey embryos in a recent publication (Nakamura et al., supra). The squamous side of the asymmetric cyst, in contrast, is composed of a flattened, differentiated epithelium that we recently identified as early human amnion-like tissue (Example 1). Indeed, TFAP2A and GATA3—two markers for hPSC-derived early human amnion—are expressed only in squamous cells (FIG. 6f). qRT-PCR analysis shows high mRNA levels for TFAP2A and GATA3 in week 16-17 human fetal amniotic epithelium, further supporting the contention that TFAP2A+/GATA3+ squamous cells molecularly resemble early human amniotic cells. Together, these results show that hPSCs can spontaneously self-organize to form asymmetric epithelial cysts that recapitulate the pen-implantation amniotic sac in human embryos, featuring an amniotic cavity lined by bipolar amnion-epiblast patterning. Such hPSC-derived asymmetric cysts are thus termed amniotic sac embryoids (ASEs) henceforth.

Figure 6G:
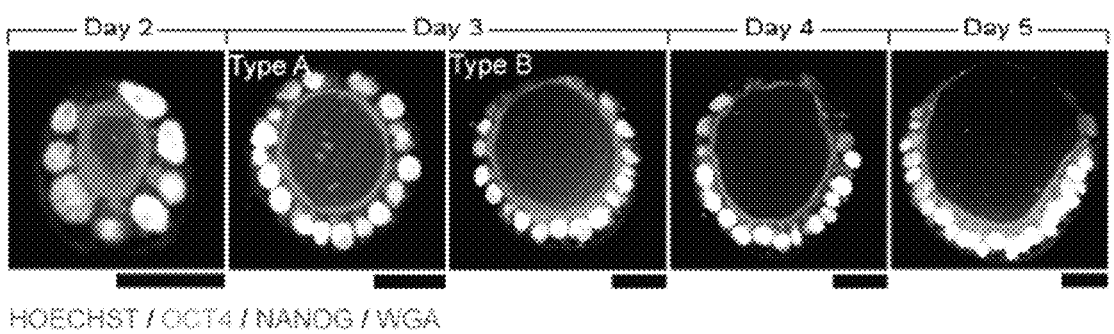
Figure 6H:
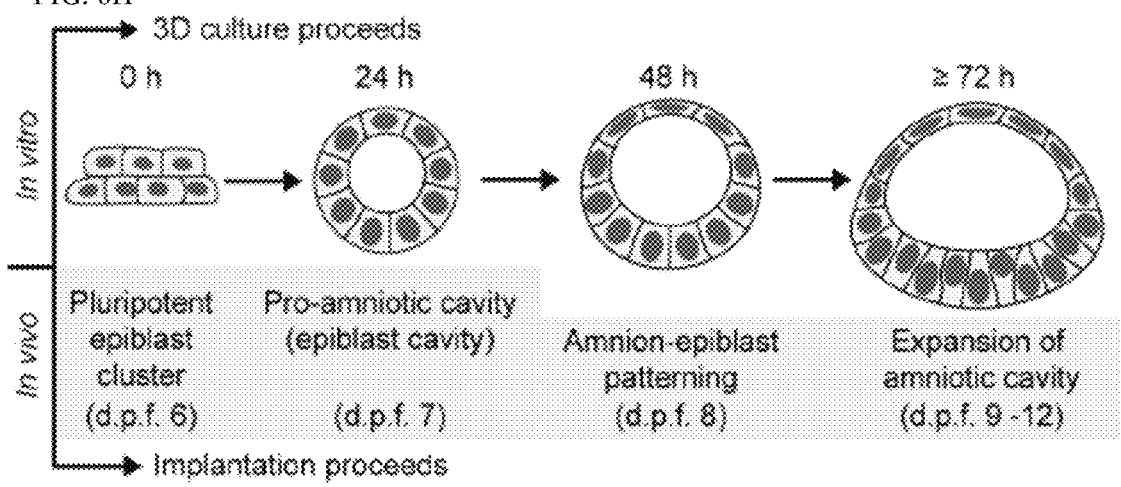
Figures 7A, 7B, 7C:
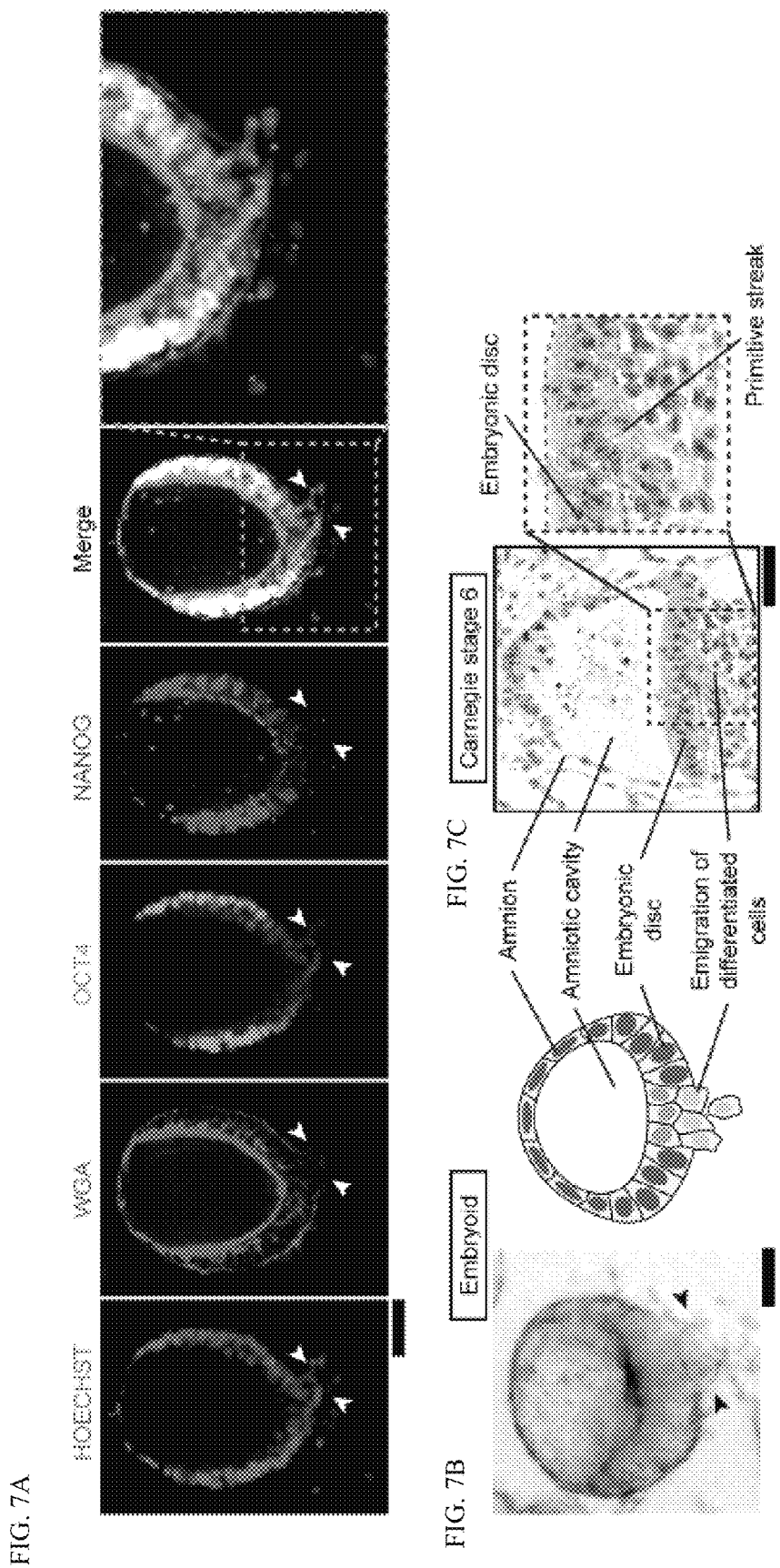
FIG. 7 shows ASEs to model progressive, posteriorizing primitive streak (PS) development. (a) Confocal micrographs showing cells emigrating from the embryonic disc of an ASE on day 5. (b) Phase contrast image (left) showing a representative ASE exhibiting cell dissemination (marked by arrowheads) from the columnar embryonic disc. (c) Carnegie stage 6 human embryo section showing the PS. (d&e) Confocal micrographs showing ASEs with different spatial patterning of BRACHYURY (BRA), OCT4 (d), and CDX2 (e) on day 5. (f) Confocal micrographs showing time dependent, stage-wise spatial patterning of BRA and ECAD in ASEs from day 3-5. (g) Cartoon summarizing the three sequential stages of ASE development that resembles progressive PS development. Scale bars in a-f, 50 µm.

The time course of ASE development was next investigated. On day 2, most hPSCs form cysts that express both OCT4 and NANOG (FIG. 6g). At this point, some cysts present an eccentrically positioned lumenal cavity; this represents the earliest stage of ASE development and resembles Carnegie stage 5a-1 (d.p.f: 7) embryo featuring a pro-amniotic cavity surrounded by polarized epiblast. On day 3, two types of ASEs are present: one (type A, 20/46) exhibits slight loss of NANOG, but not OCT4, at the flattened amniotic pole, while the other (type B, 6/46) shows significant loss of both NANOG and OCT4, and a more flattened amniotic pole (FIG. 6g). Together, day 3 ASEs exhibit the initiation and establishment of amnionepiblast patterning in vitro and appear to recapitulate Carnegie stage 5a-2 (d.p.f. 8) embryo. From day 4-5, ASEs maintain the amnion-epiblast patterning (FIG. 6g) and resemble the growing amniotic sac from Carnegie stage 5a-2 to 5b (d.p.f. 9) and 5c (d.p.f. 12). The ASE development therefore resembles the progressive morphogenesis and cell-fate patterning during pen-implantation human amniotic sac development (FIG. 6h). In support of such contention, a similar morphogenesis and OCT4/NANOG patterning in cynomolgus monkey embryos from E11-E15 were reported recently (Sasaki et al., supra). On day 5, some ASEs (96/304) exhibit an additional phenotype, with cells focally emigrating from, and only from, the embryonic disc lining the columnar pole (FIG. 7a,b). Epithelial structure and OCT4/NANOG expression are disrupted around the cell egression site (FIG. 7a).

Morphologically, these locally emerging cells resemble primitive streak (PS) initiation in Carnegie stage 6 embryos13 (FIG. 7b,c).

Figure 7E:
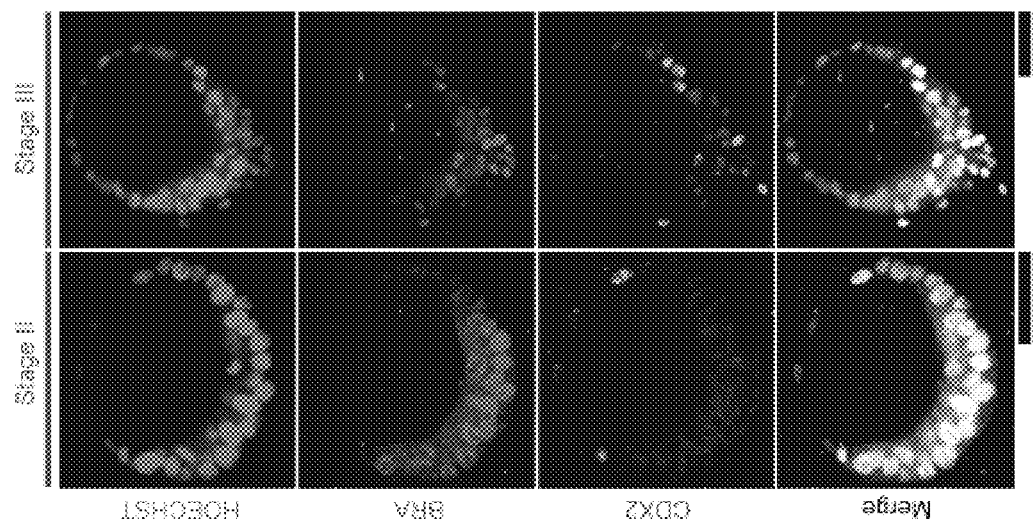
Figure 7D:
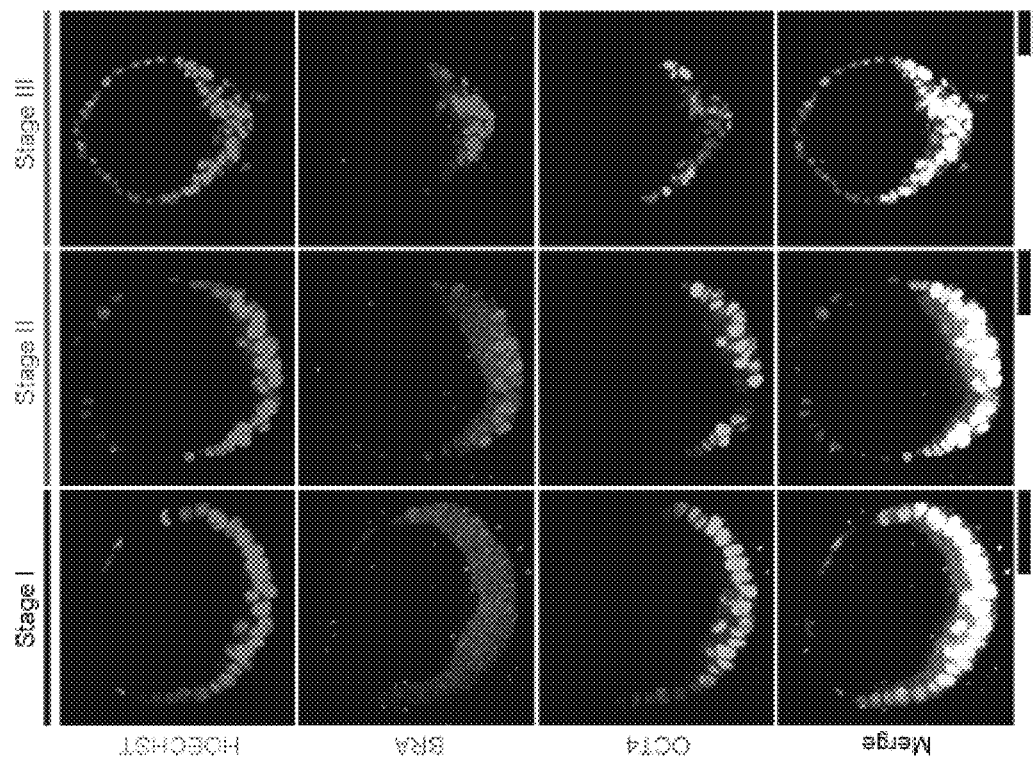

To molecularly assess such gastrulation-mimicking development of ASEs, the expression of BRACHYURY (BRA), a transcription factor associated with PS development (Bernardo, A. S., et al. Cell Stem Cell 9, 144-155 (2011)) was examined in day 5 ASEs. Three distinct patterns of BRA expression based on three consecutive stages of ASE development (FIG. 7d) were defined. Stage I (59/173) depicts ASEs that exhibit no cell dissemination and no prominent nuclear BRA in the embryonic disc. Stage II (56/173) defines ASEs that express nuclear BRA in the embryonic disc, but without cell emigration. Stage III (58/173) describes ASEs that show cells emigrating from a BRA+, PS-like region flanked by the embryonic disc (FIG. 7d). Immunofluorescence analysis of OCT4 confirms a stage-wise loss of pluripotency that parallelizes the formation of the BRA+, PS-like region (FIG. 7d). Such stage-dependent modulation of OCT4 and BRA, and the correlated phenotypic change in ASEs, resemble the PS development in post-implantation monkey embryos reported in recent publications (Nakamura et al., supra; Sasaki et al., supra). CDX2, a marker for posterior/late PS15, is expressed in the PS-like region in stage III, but not stage II, ASEs (FIG. 7e).

Such CDX2 expression in emigrating cells is also consistent with the single-cell transcriptome recently reported for gastrulating cells in monkey embryos (Nakamura at al., supra). Instead, for stage II ASEs, CDX2 is only expressed at the amniotic pole (FIG. 7e), consistent with recent finding of CDX2 as an early human amnion marker. In contrast, FOXA2—a marker for anterior PS/endoderm (Mendjan, S., et al. *Cell Stem Cell* 15, 310-325 (2014); Faial, T., et al. *Development* 142, 2121-2135 (2015)) was absent in all ASEs. GATA6, a primitive endoderm marker, was also not found in ASEs. It was observed that in vivo-like streak elongation was not observed in ASEs. Together, the molecular profile of day 5 ASEs shows that stage I ASEs mimic peri-implantation, pre-PS amniotic sac, stage II ASEs resemble early PS initiation, and stage III ASEs model posterior PS patterning.

Figures 7F, 7G:
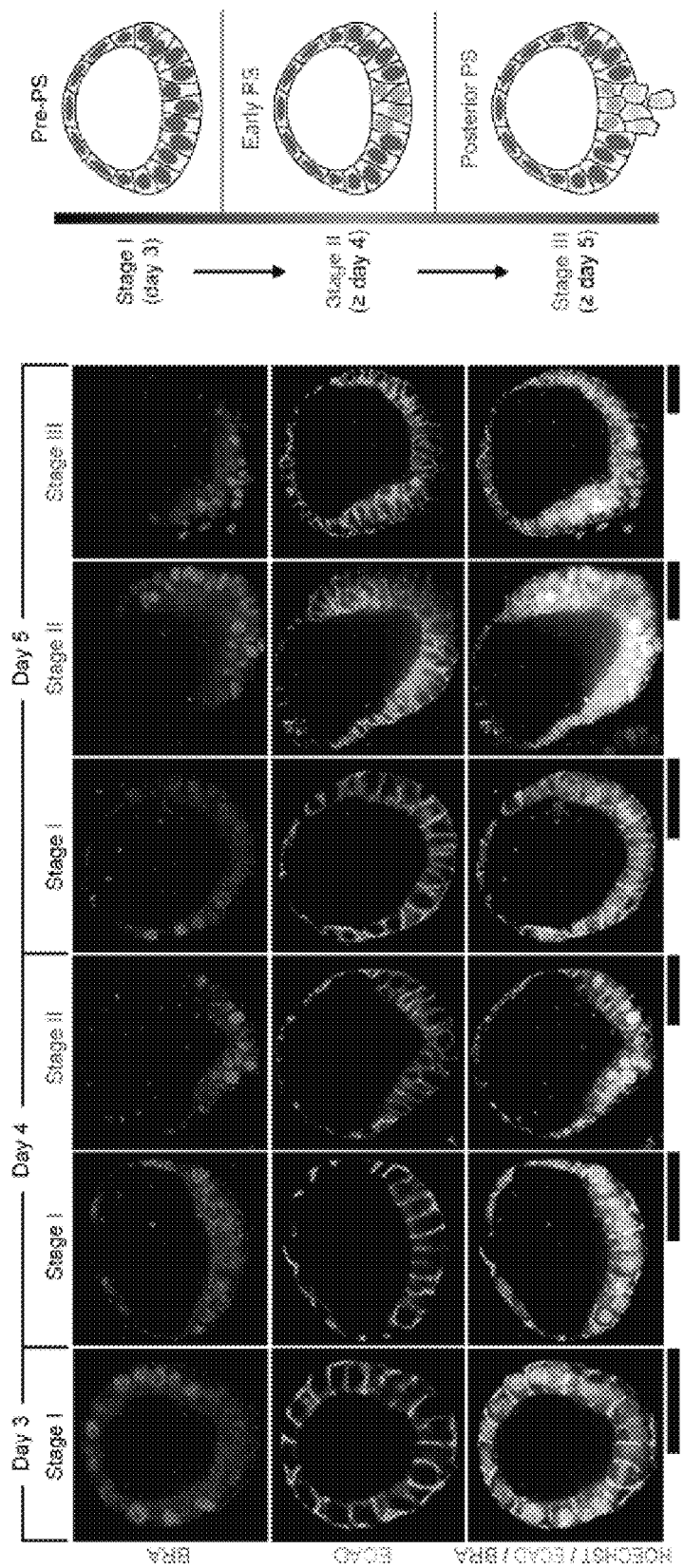

The dynamic BRA expression was traced during ASE development. On day 3, only stage I ASEs are observed, with nuclear BRA evident only at the flattened amniotic side (FIG. 7f), consistent with both a recent study identifying BRA as an early human amnion marker and another recent study reporting BRA expression in nascent monkey amnion (Sasaki et al., supra). By day 4, nuclear BRA emerges in the embryonic disc in some, but not all (13/38), ASEs, showing asynchronous advances to stage II and PS initiation (FIG. 7f). Stage III ASEs with BRA+, single emigrating cells are only evident on day 5 (FIG. 7f). ECAD is concurrently lost in the BRA+, PS-like region of stages II and III ASEs (FIG. 7f), consistent with a canonical epithelial-to-mesenchymal transition (EMT) during PS development. SNAIL, another transcription factor associated with EMT and PS development was also observed in the PS-like region of stage III ASEs. Together, these results show that ASEs can develop beyond the peri-implantation, pre-PS stage to model a progressive, posteriorizing PS development in vitro with in vivo-like sequential order (FIG. 7g).

Figure 8:
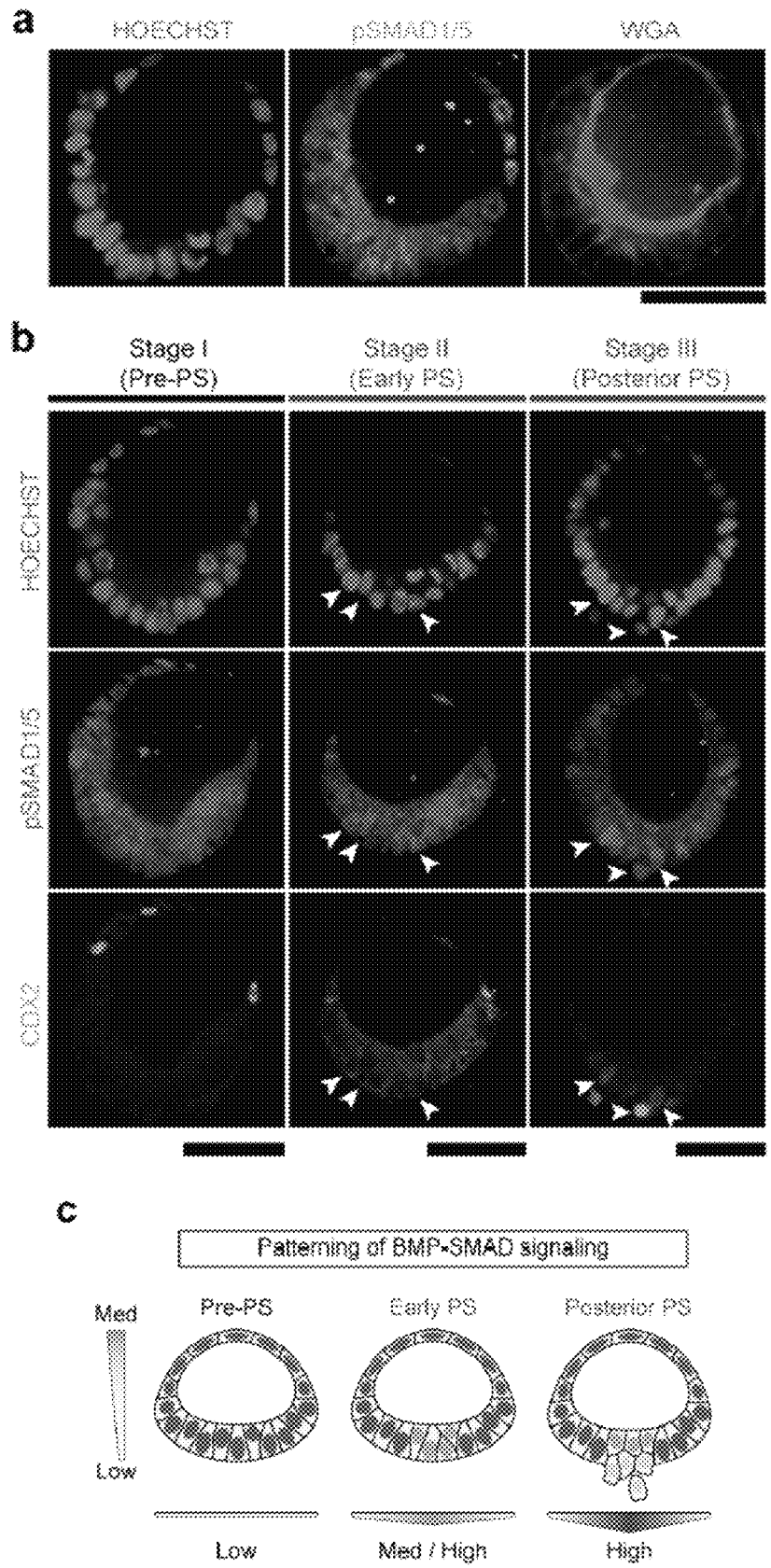
FIG. 8 shows patterned BMP-SMAD signaling in ASEs. (a) Confocal micrographs showing a pen-implantation ASE on day 5 stained for pSMAD1/5 and WGA. (b) Confocal micrographs showing stage-wise spatial patterning of pSMAD1/5 and CDX2 in ASEs on day 5. (c) Cartoon summarizing spatial patterning of BMP-SMAD signaling in the ASE along the amnion-epiblast axis as well as along the medial-lateral axis of the embryonic disc.
Figure 9:
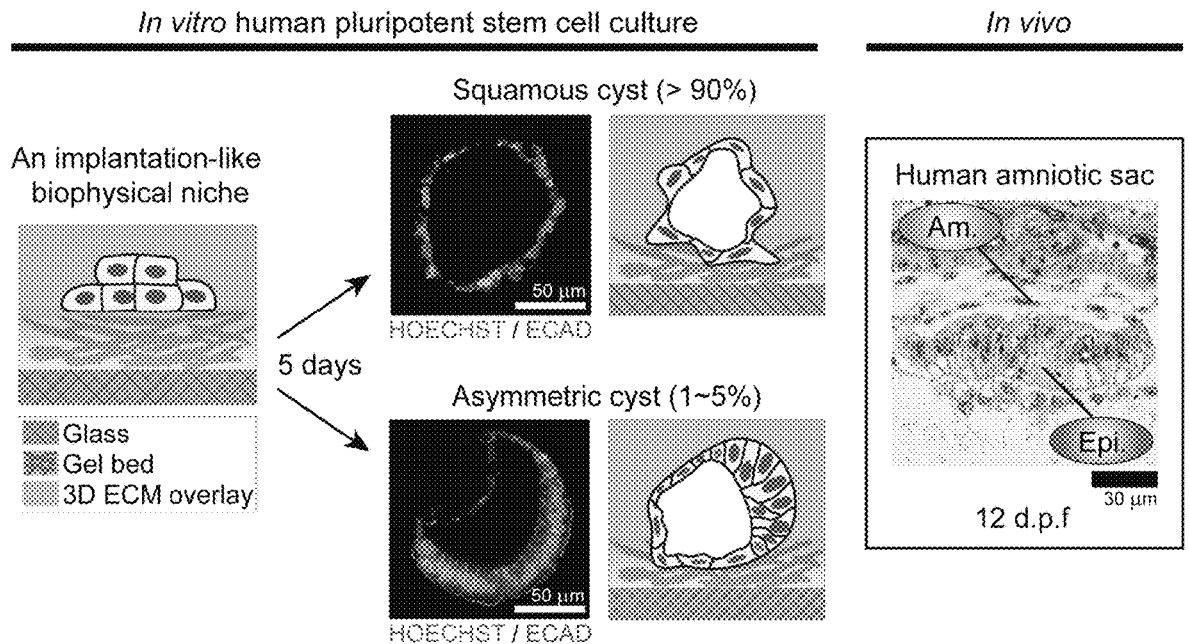
FIG. 9 shows an overview of using bioengineered, human pluripotent stem cell (hPSC) culture system in vitro for modeling pen-implantation development of human amnion and human amniotic sac. (Left) To mimic the soft tissue bed and the 3D extracellular matrix (ECM) environment surrounding the pen-implantation human embryo, a Gel-3D culture system was developed. (Right) Section shows a pen-implantation human embryol. Am.: amnion, Epi: epiblast. Scale bar, 50 µm (left), 30 µm (right).
Figure 10:
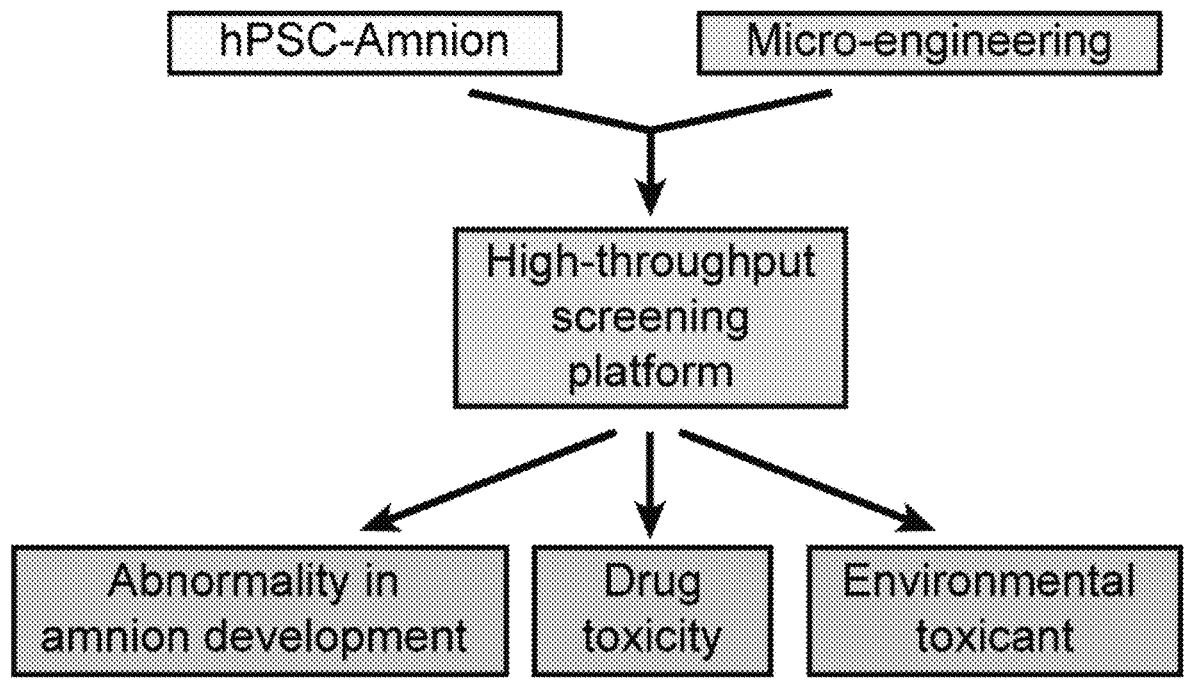
FIG. 10 shows a flow chart of an exemplary micro-engineered human amniotic tissue array that uses a micro-scale array of human amniotic tissues to enable high-throughput screening for developmental abnormalities, toxicity of drugs, and environmental hazards.
Figure 11:
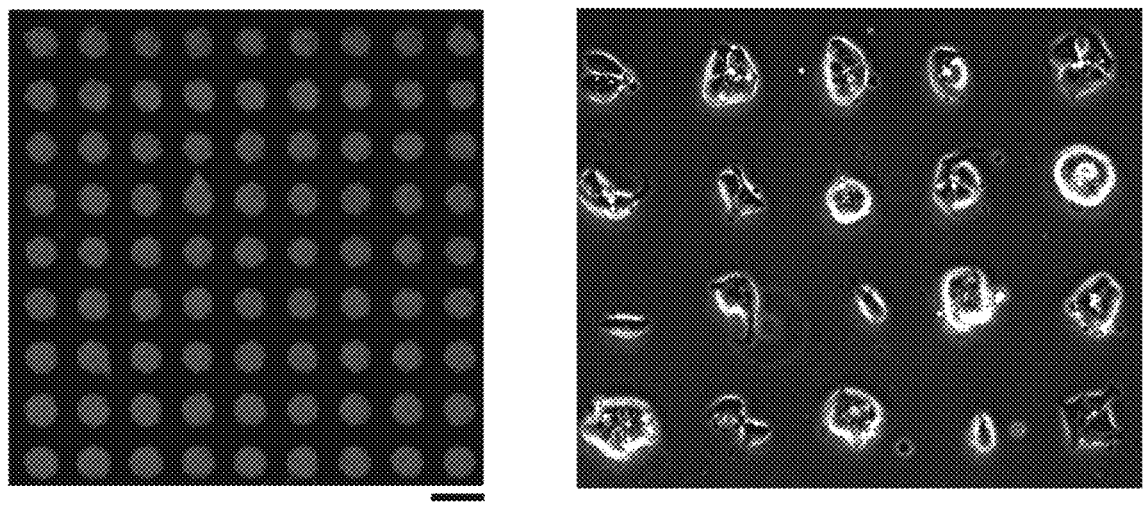
FIG. 11 shows patterning of hPSCs using micro-engineered ECM array. (Left) Confocal micrograph showing the staining of LAMININ in the micro-contact printed array of Geltrex. Scale bar, 100 µm. (Right) Phase contrast image showing hPSCs attaching and confined to the micro-contact printed protein array.
Figure 12:
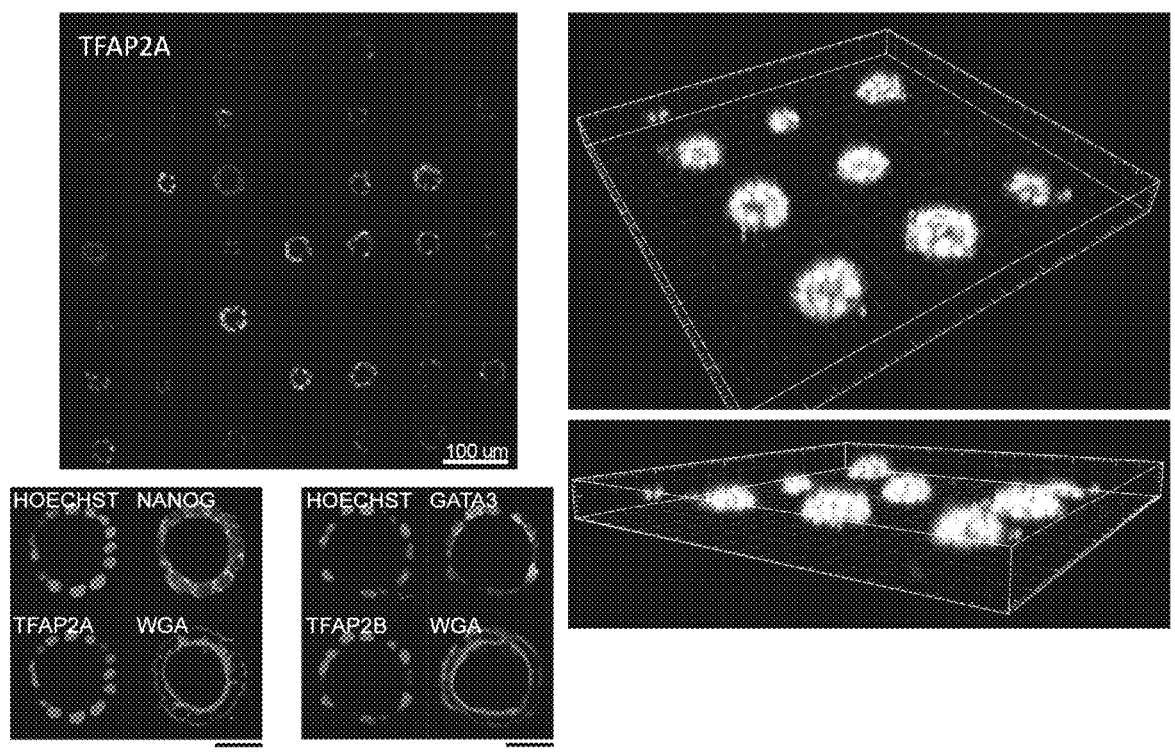
FIG. 12 shows a micro-engineered human amniotic tissue array. (Upper left) Confocal micrograph showing the staining of amniotic marker TFAP2A in the cysts formed on the Geltrex ECM array. Scale bar, 100 µm. (Lower left) Confocal micrographs showing the staining of HOECHT, NANOG/GATA3, TFAP2A, and WGA in a representative cyst cultured on the micro-engineered ECM array at day 3. Scale bar, 30 µm. (Right) 3D renderings of confocal micrograph showing the staining of HOECHST, TFAP2A, and WGA, in the amniotic tissue array.

During early embryogenesis, BMP-SMAD signaling plays a pivotal role in tissue specification and morphogenesis, as loss of Bmp2 or Smad5 results in defects in both amniotic and embryonic patterning in mice (Zhang, H. B. and Bradley, A. *Development* 122, 2977-2986 (1996); Chang, H., et al. *Development* 126, 1631-1642 (1999)). It was recently found that BMP-SMAD signaling is required for amniogenesis, as treatment by small molecule BMP inhibitor or BMP antagonist NOGGIN could inhibit amniogenic differentiation. Thus, BMP-SMAD signaling during ASE development was examined. Immunofluorescence analysis of phosphorylated SMAD1/5 (pSMAD1/5)—a downstream target and activator of BMP-SMAD signaling—shows prominent nuclear pSMAD1/5 only at the amniotic pole of pen-implantation (stage I) ASEs (FIG. 8a). Stage-dependent patterning of pSMAD1/5 was further observed (FIG. 8b), mirroring the progressive BRA expression patterning during ASE development (FIG. 7d,f). Notably, nuclear pSMAD1/5 emerges in the embryonic disc prior to CDX2 (FIG. 8b), consistent with the recent finding that BMP-SMAD signaling activation precedes CDX2-mediated posterior PS specification (Faial et al., supra). Together, these results provide direct evidence for endogenous, stage-dependent patterning of BMP-SMAD signaling during ASE development in vitro (FIG. 8c).

In this study, it was shown that hPSCs can self-organize to model human amniotic sac development at implantation and beyond in a biomimetic 3D culture system. Although long-established textbook dogma advocates that human amniotic sac development involves an intermediate step in which the epiblast cyst is opened to the trophoblast, forming a tropho-epiblastic cavity (d.p.f. 8) (Schoenwolf, G. C., Bleyl, S. B., Brauer, P. R. and Francis-West, P. H. Larsen's human embryology. Churchill Livingstone/Elsevier, 576 (2014), the data presented herein shows otherwise—human amniotic sac develops as a continuous epithelial cyst that constantly encloses the (pro-)amniotic cavity during amniogenesis and amnion-epiblast patterning. The ASE develops in the absence of other extraembryonic tissues and activates endogenous patterning of BMPSMAD signaling, showing a potential self-patterning nature of human amniotic sac development.

The findings not only unveil a new developmental potential of hPSCs, but also provide new understanding of human development at implantation and early gastrulation. Together, this work generates a new model—the ASE—for investigating early human embryogenesis, complementing scarce in vivo studies to advance human embryology and reproductive medicine.

Example 3

Model of Peri-Implantation Human Embryonic Development

This example describes a method for modeling early human developmental events in vitro. Described in FIGS. 9-14 is a customized and specialized technology for applying the hPSC-amnion technology described in Examples 1 and 2 for high-throughput screening in regenerative medicine and defined modeling and study of early embryonic induction. In some embodiments, methods utilize a microfluidic interaction device as described (See e.g., Zheng et al., *Adv. Healthcare Mater* 2016, 5, 1014-1024) or other microfluidic device.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method for preparing amnion-like tissue comprising:
 a) contacting cells selected from a group consisting of human induced pluripotent stem cells (hiPSCs) and human embryonic stem cells (hESCs) on a solid support coated with a gel matrix with a thickness of 100 μm, and a Young's bulk modulus of 900 Pa, comprising microposts with a height of 8.4 μm;
 b) culturing said hiPSCs or hESCs in a medium comprising Rho-kinase (ROCK) inhibitor Y-2763212 for 24 hours;
 c) coating said cells on a said solid support with further gel matrix such that said cells are surrounded by said gel matrix after step b);
 d) replacing said Y-2763212 medium with a Y-2763212-free medium, and
 e) culturing said hiPSCs or hESCs for 5 days under conditions such that amnion-like tissue is generated, wherein said amnion-like tissue comprises a squamous cyst comprising an epithelium, wherein said squamous cyst does not express NANOG, OCT, or SOX.

2. The method of claim 1, wherein said gel matrix is a natural or synthetic polymeric hydrogel.

3. The method of claim 2, wherein said gel matrix is growth factor basement membrane matrix or a solubilized basement membrane preparation extracted from the Engelbreth-Holm-Swarm (EHS) mouse sarcoma.

4. The method of claim 1, wherein said amnion-like tissue is an asymmetric cyst comprising a columnar portion and said squamous cyst.

5. The method of claim 1, wherein said amnion-like tissue is generated in a device comprising parallel first, second, and third channels wherein said first and second channels are cell channels comprising a loading reservoir operably linked to said third channel comprising a gel interaction matrix.

6. The method of claim 1, wherein said amnion-like tissue expresses one or more markers selected from the group consisting of ITGB6, VTCN1, GABRP, MUC16, HAND1, POSTN, TFAP2A, TFAP2B, KRT17 and KRT18.

* * * * *